US009834578B2

(12) United States Patent
Yue et al.

(10) Patent No.: US 9,834,578 B2
(45) Date of Patent: Dec. 5, 2017

(54) ENHANCED SENSITIVITY FOR ANALYSIS OF KETOSTEROID COMPOUNDS USING MASS SPECTROMETRY

(75) Inventors: Bingfang Yue, Cedar Hills, UT (US); Alan L. Rockwood, Riverton, UT (US); Mark M. Kushnir, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 520 days.

(21) Appl. No.: 13/114,885

(22) Filed: May 24, 2011

(65) Prior Publication Data

US 2012/0126107 A1 May 24, 2012

Related U.S. Application Data

(60) Provisional application No. 61/349,138, filed on May 27, 2010.

(51) Int. Cl.
*C07J 1/00* (2006.01)
*C07J 41/00* (2006.01)

(52) U.S. Cl.
CPC ......... *C07J 1/0022* (2013.01); *C07J 41/0016* (2013.01)

(58) Field of Classification Search
CPC ..................... C07J 41/0016; C07J 1/0022
USPC ................... 436/71, 128, 161, 173
See application file for complete search history.

(56) References Cited

U.S. PATENT DOCUMENTS 5,491,071 A * 2/1996 Adamczyk et al. ............ 435/25
6,410,700 B1 * 6/2002 Williams et al. ............ 536/18.7
6,977,143 B1 * 12/2005 Caulfield et al. ................. 435/4
7,473,560 B2 * 1/2009 Soldin ........................... 436/173
7,804,063 B2 * 9/2010 Ghoshal et al. .............. 250/282
7,807,472 B2 * 10/2010 Xu et al. ........................ 436/87

(Continued)

OTHER PUBLICATIONS

Phillips, V. A. et al, Journal of Agricultural and Food Chemistry 1990, 38, 525-528.*

(Continued)

*Primary Examiner* — Arlen Soderquist
(74) *Attorney, Agent, or Firm* — Thorpe North and Western, LLP; Todd B. Alder

(57) ABSTRACT

The present disclosure provides methods and composition involving increased sensitivity of compounds using mass spectrometry. In one embodiment, a method of increasing the sensitivity for detection of a carbonyl group-containing compound by mass spectrometry can comprise derivatizing the carbonyl group-containing compound with an O-substituted hydroxylamine thereby producing an oxime, resulting in enhanced sensitivity of detection by mass spectrometry, as compared to the underivatized carbonyl group-containing compound.

Additionally, a method for assaying a carbonyl group-containing compound can comprise reacting the carbonyl group-containing compound in a sample with an O-substituted hydroxylamine to produce an oxime and performing analysis with mass spectrometric detection of the oxime by a mass spectrometry instrument.

Further, an assay for a ketosteroid can comprise a derivatized ketosteroid produced by reacting the ketosteroid with an O-substituted hydroxylamine to produce an oxime and a mass spectrometry instrument for performing mass spectrometric analysis on the derivatized ketosteroid.

14 Claims, 15 Drawing Sheets

(56) References Cited

U.S. PATENT DOCUMENTS

| | | | | |
|---|---|---|---|---|
| 7,935,921 | B2* | 5/2011 | Grant et al. | 250/288 |
| 8,153,962 | B2* | 4/2012 | Ghoshal et al. | 250/282 |
| 8,158,931 | B2* | 4/2012 | Ghoshal et al. | 250/282 |
| 8,372,653 | B2* | 2/2013 | Dey et al. | 436/173 |
| 2004/0235193 | A1* | 11/2004 | Soldin | 436/518 |
| 2006/0040256 | A1* | 2/2006 | Caulfield et al. | 435/4 |
| 2007/0141624 | A1* | 6/2007 | Winn | 435/7.1 |
| 2007/0275935 | A1* | 11/2007 | Stewart et al. | 514/169 |
| 2009/0155179 | A1* | 6/2009 | Hellerstein et al. | 424/9.2 |
| 2009/0215111 | A1* | 8/2009 | Veenstra et al. | 435/40.52 |
| 2010/0155595 | A1* | 6/2010 | Ghoshal et al. | 250/283 |
| 2011/0003395 | A1* | 1/2011 | Dey et al. | 436/98 |

OTHER PUBLICATIONS

Rosenfeld, J. M. et al, Analytical Chemistry 1991, 63, 1536-1541.*
Liu, S. et al, Rapid Communications in Mass Spectrometry 2000, 14, 390-400.*
Venhuis, B. J. et al, Journal of Medicinal CHemistry 2003, 46, 4136-4140.*
Liu, S. et al, Analytical Chemistry 2003, 75, 5835-5846.*
Wichard, T. et al, Journal of Chromatography B 2005, 814, 155-161.*
Kushnir, M. M. et al, Clinical Chemistry 2006, 52, 120-128.*
Byrns, M. C. et al, Chemical Research in Toxicology 2006, 19, 414-420.*
Kalhorn, T. F. et al, Rapid Communications in Mass Spectrometry 2007, 21, 3200-3206.*
Huang, G. et al, Analytical Chemistry 2007, 79, 8327-8332.*
Licea-Perez, H. et al, Steroids 2008, 73, 601-610.*
Nambara, T. et al, Journal of Chromatography 1976, 118, 127-133.*
Fitzpatrick, F. A., Analytical Chemistry 1977, 50, 47-51.*
Brown, D. S. et al, Tetrahedron 1995, 51, 11473-11488.*
Shimada, K. et al, Journal of Liquid Chromatography & Related Technologies 1998, 21, 765-775.*
Moody, C. J. et al, Journal of organic Chemistry 1999, 64, 4419-4425.*
Mamalis, P. et al, Journal of the Chemical Society 1962, 3915-3926.*
Dieter, R. K. et al, Canadian Journal of Chemistry 1993, 71, 814-823.*
Kolasa, T. et al, Journal of Medicinal Chemistry 2000, 43, 690-705.*
Maillard, L. T. et al, Journal of Organic Chemistry 2005, 70, 6303-6312.*
Major, R. T. et al, journal of Medicinal and Pharmaceutical Chemistry 1961, 4, 51-65.*
Mollin, J. et al, Chemicke Zvesti 1975, 29, 39-43.*
Koshy, T. K. et al, Journal of Chromatographic Science 1975, 13, 97-104.*
Brooks, C. J. W. et al, Journal of Chromatography 1975, 112, 499-511.*
Nambara, T. et al, Journal of Chromatography 1975, 114, 81-86.*
Fitzpatrick, F. A. et al, Analytical Chemistry 1977, 49, 1032-1035.*
Hirsch, A. F. et al, Journal of Medicinal Chemistry 1977, 20, 1546-1551.*
Brooks, C. J. W. et al, in "practical Mass Spectromtery", Middleditch, B.S. editor, 1979, Plenum Press, New York, 57-126.*
Schweer, H., Journal of Chromatography 1982, 236, 355-360.*
Schweer, H., Journal of Chromatography 1982, 236, 361-367.*
Biondi, P, A. et al, Journal of Chromatography 1987, 411, 275-284.*
Biondi, P, A. et al, Journal of Chromatography 1989, 467, 315-320.*
Andrews, M. A., Carbohydrate Research 1989, 194, 1-19.*
Andrews, M. A. et al, Carbohydrate Research 1990, 199, 183-194.*
Mallet, A. I. et al, Journal of Chromatography 1991, 562, 647-658.*
Goto, J. et al, Journal of Chromatography 1991, 567, 343-349.*
Kwan, T. K. et al, Journal of Steroid Biochemistry and Molecular Biology 1992, 43, 549-556.*
Mikola, H. et al, Steroids 1993, 58, 330-334.*
Chou, C.-C. et al, Journal of Agriculture and Food Chemistry 1994, 42, 2225-2230.*
de Boer, D. et al, Journal of Mass spectromtry 1995, 30, 497-504.*
Biondi, P. A. et al, Journal of Chromatography A 1996, 726, 246-252.*
Selley, M. L., Journal of Chromatography B 1997, 691, 263-268.*
Gower, D. B. et al, Journal of Steroid Biochemistry and Molecular Biology 1997, 63, 81-89.*
Wiesenthal, K. et al, Journal of AOAC International, 2000, 83, 859-869.*
de Lijser, H. J. P. et al, Journal of Organic Chemistry 2004, 69, 3057-3067.*
de Lijser, H. J. P. et al, Journal of Organic Chemistry 2007, 72, 4126-4134.*
Shibata, Y. et al, Prostate 2000, 42, 45-55.*
Mitamura, K. et al, Chromatography 2001, 22, 11-15.*
Zhao, M. et al, Steroids 2004, 69, 721-726.*
Niwa, M. et al, Journal of Chromatography B 2005, 824, 258-266.*
Moffett, R. B. et al, Journal of Heterocyclic Chemistry 1979, 16, 1459-1467.*
Brown, P. et al, Journal of the Chemical Society, Perkins Transactions 1 1991, 881-891.*
Gallagher, P. T. et al, Journal of the Chemical Society, Perkins Transactions 1 1997, 2633-2637.*
Polyakov, V. A. et al, Journal of Physical Organic Chemistry 1999, 12, 357-363.*

* cited by examiner

ENHANCED SENSITIVITY FOR ANALYSIS OF KETOSTEROID COMPOUNDS USING MASS SPECTROMETRY

CROSS-REFERENCE TO RELATED APPLICATIONS AND CLAIM OF PRIORITY

This application claims the benefit of U.S. Provisional Patent Application Ser. No. 61/349,138 filed on May 27, 2010, which is hereby incorporated by reference in its entirety.

BACKGROUND

Mass spectrometry (MS) is an analytical technique for the determination of the elemental composition of a sample or molecule. It is also used for elucidating the chemical structures of molecules, such as peptides and other chemical compounds. The MS principle consists of ionizing chemical compounds to generate charged molecules or molecule fragments and measurement of their mass-to-charge ratios (m/z).

Mass spectrometry can be coupled with other analytical techniques such as gas chromatography, liquid chromatography, etc., allowing for analysis and separation of a mixture of compounds.

Various mass spectrometry techniques include gas chromatography coupled with mass spectrometry (GC-MS), liquid chromatography mass spectrometry (LC-MS), tandem mass spectrometry (MS/MS), liquid chromatography tandem mass spectrometry (LC-MS/MS), etc.

SUMMARY

The following disclosure provides methods and composition involving increased sensitivity for compounds using mass spectrometry. In one embodiment, a method of increasing the sensitivity for detection of a carbonyl group-containing compound by mass spectrometry can comprise derivatizing the carbonyl group-containing compound with an O-substituted hydroxylamine thereby producing an oxime, resulting in enhanced sensitivity of detection by mass spectrometry, as compared to the underivatized carbonyl group-containing compound.

In another embodiment, a derivatized carbonyl group-containing compound can be manufactured by the process of derivatizing the carbonyl group-containing compound with an O-substituted hydroxylamine to produce an oxime, having enhanced sensitivity of detection by mass spectrometry as compared to the carbonyl group-containing compound without derivatization, wherein the enhanced sensitivity of detection is measured as an increase of ion signal acquired.

Additionally, a method for assaying a carbonyl group-containing compound can comprise reacting the carbonyl group-containing compound in a sample with an O-substituted hydroxylamine to produce an oxime and performing analysis with mass spectrometric detection of the oxime by a mass spectrometry instrument.

In one embodiment, an assay for a ketosteroid can comprise a derivatized ketosteroid produced by reacting the ketosteroid with an O-substituted hydroxylamine to produce an oxime and a mass spectrometry instrument for performing mass spectrometric analysis on the derivatized ketosteroid.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

DETAILED DESCRIPTION

Figure 1:
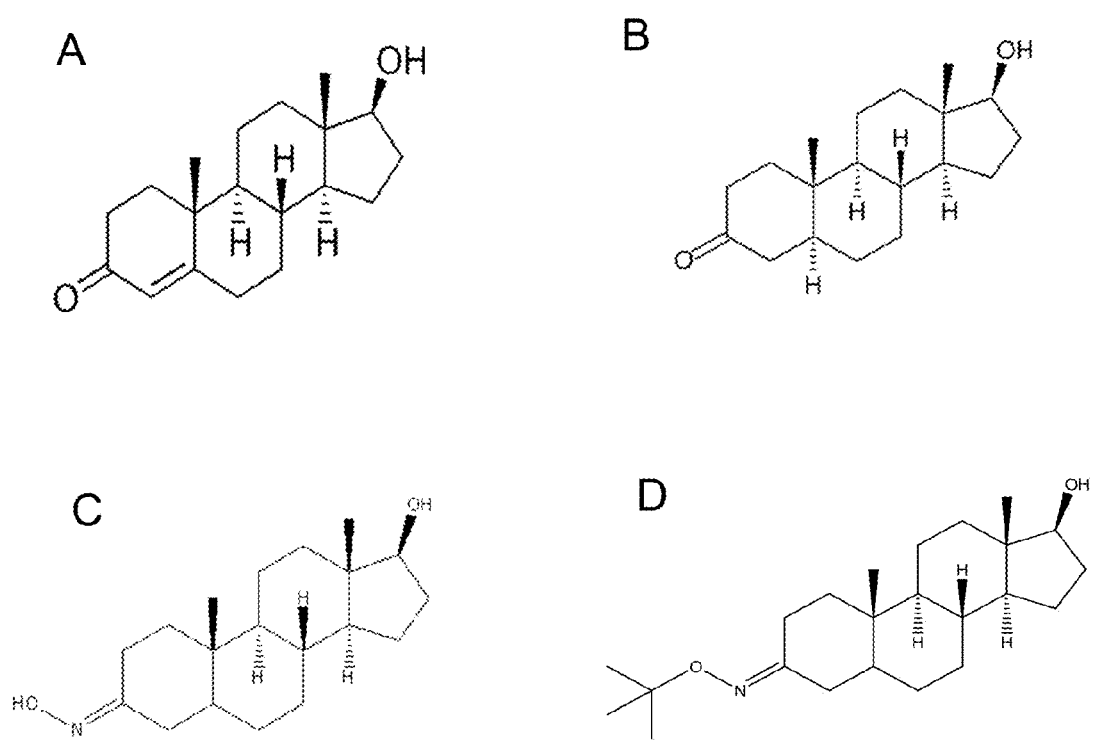
FIGS. 1A-D show molecular structures of (A) T, (B) DHT, (C) DHT oxime by hydroxylamine, (D) DHT oxime by O-tert-butyl-hydroxylamine in accordance with an embodiment of the present invention.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

Definitions

In describing and claiming the present invention, the following terminology will be used.

The singular forms "a," "an," and "the" include plural referents unless the context clearly dictates otherwise. Thus, for example, reference to "a compound" includes reference to one or more of such compounds and reference to a step of "forming" refers to one or more of such steps.

As used herein, "substituted" means that a hydrogen atom of a compound or moiety is replaced by another atom such as a carbon atom or a heteroatom, which is part of a group referred to as a substituent. Substituents include, for example and without limitation, alkyl, alkoxy, aryl, aryloxy, alkenyl, alkenoxy, alkynyl, alkynoxy, thioalkyl, thioalkenyl, thioalkynyl, and thioaryl.

As used herein, "heteroatom" refers to a non-carbon atom and can include, without limitation, nitrogen, oxygen, phosphorus or sulfur. The terms "halo" and "halogen" refer to a fluoro, chloro, bromo, or iodo substituent.

As used herein, "alkyl" refers to a branched, unbranched, or cyclic saturated hydrocarbon group, which typically, although not necessarily, contains from 1 to about 50 carbon atoms, or 1 to about 40 carbon atoms, or 1 to about 30 carbon atoms for example. Alkyls include, but are not limited to, methyl, ethyl, n-propyl, isopropyl, n-butyl, isobutyl, t-butyl, octyl, and decyl, for example, as well as cycloalkyl groups such as cyclopentyl, and cyclohexyl, for example. The term "lower alkyl" refers to an alkyl group having from 1 to 6 carbon atoms. The term "higher alkyl" refers to an alkyl group having more than 6 carbon atoms, for example, 7 to about 50 carbon atoms, or 7 to about 40 carbon atoms, or 7 to about 30 carbon atoms or more. As used herein, "substituted alkyl" refers to an alkyl substituted with one or more substituent groups. The term "heteroalkyl" refers to an alkyl in which at least one carbon atom is replaced with a heteroatom. If not otherwise indicated, the term "alkyl" includes unsubstituted alkyl, substituted alkyl, lower alkyl, and heteroalkyl.

As used herein, "aryl" refers to a group containing a single aromatic ring or multiple aromatic rings that are fused together, directly linked, or indirectly linked (such that the different aromatic rings are bound to a common group such as a methylene or ethylene moiety). Aryl groups described herein may contain, but are not limited to, from 5 to about 50 carbon atoms, or 5 to about 40 carbon atoms, or 5 to 30 carbon atoms or more. Aryl groups include, for example, phenyl, naphthyl, anthryl, phenanthryl, biphenyl, diphenylether, diphenylamine, and benzophenone. The term "substituted aryl" refers to an aryl group comprising one or more substituent groups. The term "heteroaryl" refers to an aryl group in which at least one carbon atom is replaced with a heteroatom. If not otherwise indicated, the term "aryl" includes unsubstituted aryl, substituted aryl, and heteroaryl.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3.5, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described. Regarding the phrase "less than," in one embodiment, the use of such a term refers to the presence of the element in some amount; i.e., does not include zero.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

EMBODIMENTS OF THE INVENTION

The present inventors have recognized the need for improving the detectability of various organic compounds using mass spectrometry techniques. As such, the present inventors have developed methods and compositions allowing for increased detection of compounds using mass spectrometry techniques. It is noted that when discussing the present compositions, associated methods, or associated systems, each of these discussions can be considered applicable to each of these embodiments, whether or not they are explicitly discussed in the context of that embodiment. Thus, for example, in discussing a derivatized carbonyl group-containing compound, such a derivatized carbonyl group-containing compound can also be used in a method of assaying for such a compound or a method of increasing the sensitivity of a carbonyl group-containing compound, and vice versa.

In one embodiment, a method of increasing the sensitivity for detection of a carbonyl group-containing compound by mass spectrometry can comprise derivatizing the carbonyl group-containing compound with an O-substituted hydroxylamine thereby producing an oxime, resulting in enhanced sensitivity of detection by mass spectrometry, as compared to the underivatized carbonyl group-containing compound.

In another embodiment, a derivatized carbonyl group-containing compound can be manufactured by the process of derivatizing the carbonyl group-containing compound with an O-substituted hydroxylamine to produce an oxime, having enhanced sensitivity of detection by mass spectrometry as compared to the carbonyl group-containing compound without derivatization, wherein the enhanced sensitivity of detection is measured as an increase of ion signal acquired.

Additionally, a method for assaying a carbonyl group-containing compound can comprise reacting the carbonyl group-containing compound in a sample with an O-substituted hydroxylamine to produce an oxime and performing analysis with mass spectrometric detection of the oxime by a mass spectrometry instrument.

In one embodiment, an assay for a ketosteroid can comprise a derivatized ketosteroid produced by reacting the ketosteroid with an O-substituted hydroxylamine to produce an oxime and a mass spectrometry instrument for performing mass spectrometric analysis on the derivatized ketosteroid.

The O-substituted hydroxylamine can be selected from the group consisting of O-alkyl-hydroxylamine, O-silyl-hydroxylamine, O-aryl-hydroxylamine, O-phenyl-hydroxylamine, and mixtures thereof. Additionally, the O-substituted hydroxylamine can be an O-substituted branched hydroxylamine. In one embodiment, the O-substituted hydroxylamine can contain a tertiary carbon atom.

The O-alkyl-hydroxylamine can have the structure as shown in Formula I:

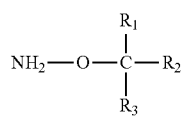

(I)

wherein $R_1$, $R_2$, and $R_3$, are, independently, linear or branched, substituted or unsubstituted, alkyl groups or hydrogen. In one example, at least two of $R_1$, $R_2$, and $R_3$ cannot be hydrogen. Additionally, the O-alkyl-hydroxyamine can be O-tert-butyl hydroxylamine.

In another embodiment, the O-aryl-hydroxylamine can have the structure as shown in Formula II:

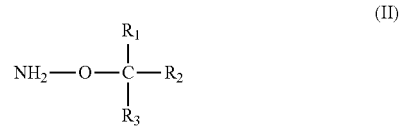

(II)

wherein $R_1$, $R_2$, and $R_3$, are, independently, linear or branched, substituted or unsubstituted, alkyl or aryl groups or hydrogen, with the proviso that at least one of the $R_1$, $R_2$, and $R_3$ groups is an aryl group. In one aspect, the O-aryl-hydroxylamine can be O-phenyl-hydroxylamine.

The O-silyl-hydroxylamine can have the structure as shown in Formula III:

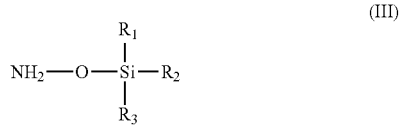

(III)

wherein $R_1$, $R_2$, and $R_3$, are, independently, linear or branched, substituted or unsubstituted, alkyl or aryl groups. In one example, at least two of $R_1$, $R_2$, and $R_3$ cannot be hydrogen.

The carbonyl compounds described herein can be any compound containing at least one carbonyl functional group. Such carbonyl groups can include ketones, aldehydes, carboxylic acids, and esters. In one embodiment, the carbonyl compound can contain a ketone. In another embodiment, the carbonyl compound can contain an aldehyde. While the carbonyl compounds can generally be any compound, in one embodiment, the carbonyl compound can be an organic compound. In another embodiment, the carbonyl compound can be a steroid. In yet another embodiment, the carbonyl compound can be a ketosteroid. In still another embodiment, the ketosteroid can be 5α-dihydrotestosterone. In one aspect, the ketosteroid can be testosterone.

Generally, the enhanced sensitivity can be measured as an increase of ion signal acquired in any mode of mass spectrometry, such as MS scan, product ion scan, selected ion monitoring, selected/multiple reaction monitoring, to name a few. The enhanced sensitivity can be due to improved ionization efficiency or improved fragmentation yield depending on the operation mode of a mass spectrometer. In one embodiment, the derivatizing can provide an increase in ion signal of greater than or equal to about 2 fold. In other embodiments, the derivatizing can provide an increase in ion signal of greater than or equal to about 5 fold, about 10 fold, about 100 fold, or about 1000 fold.

Additionally, in one embodiment, the derivatizing can provide at least about a 2 fold increase in detected ions in the top 30% of total ions detected. By "top 30% of total ions detected," the phrase refers to 30% of the heaviest ions detected during a mass spectrometry analysis. In other embodiments, the derivatizing can provide at least about a 5 fold increase, at least about a 10 fold increase, at least about a 100 fold increase, or even at least about a 1000 fold increase in detected ions in the top 30% of total ions detected.

The present compositions, methods, and systems can be used in conjunction with any type of mass spectrometry instrument and/or technique. In one embodiment, the mass spectrometry instrument can be a mass spectrometer (MS) instrument. In another embodiment, the mass spectrometry instrument can be a liquid chromatography mass spectrometry (LC/MS) instrument. In still another embodiment, the mass spectrometry instrument can be a tandem mass spectrometry (MS/MS) instrument. In still yet another embodiment, the mass spectrometry instrument can be a liquid chromatography tandem mass spectrometry (LC-MS/MS) instrument. Additionally, the mass spectrometry can be done in any operation mode, including multiple reaction monitoring (MRM) mode and/or selected ion monitoring (SIM) mode. In one embodiment, the mass spectrometry can include a full mass spectrum (using time-of-flight (TOF), orbitrap, etc.). Additionally, the present methods can include simultaneous measurement of multiple derivatized carbonyl group-containing compounds. Additionally, in some embodiments, the mass spectrometry techniques discussed herein can include matrix-assisted laser desorption/ionization (MALDI).

EXAMPLES

The following examples illustrate a number of embodiments of the present compositions, systems, and methods that are presently known. However, it is to be understood that the following are only exemplary or illustrative of the application of the principles of the present compositions, systems, and methods. Numerous modifications and alternative compositions, methods, and systems may be devised by those skilled in the art without departing from the spirit and scope of the present systems and methods. The appended claims are intended to cover such modifications and arrangements. Thus, while the present compositions, systems, and methods have been described above with particularity, the following examples provide further detail in connection with what are presently deemed to be the acceptable embodiments.

Example 1—Increased Sensitivity for DHT Study

1. DHT Derivatization

Figure 2A:
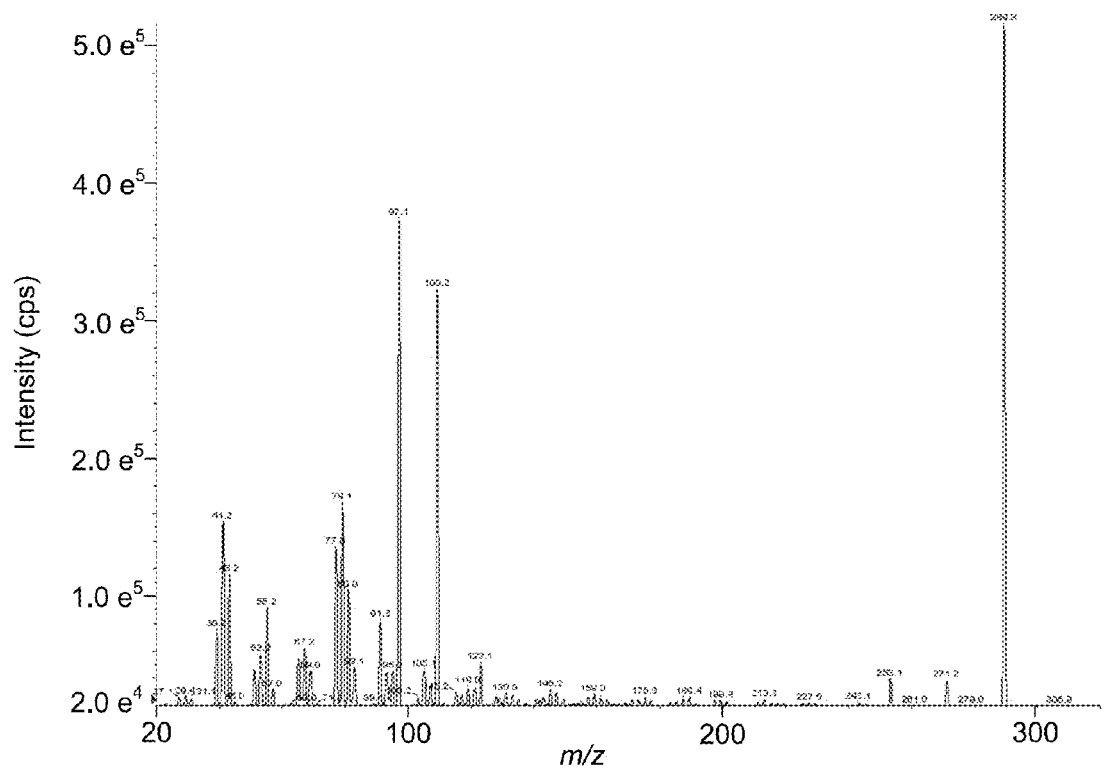
FIGS. 2A-B show MS/MS spectra of underivatized T(A) and DHT (B), with precursor ions of T and DHT are m/z 289 and m/z 291, both protonated [M+H]+ (the spectra was acquired by ramping the collisional energy (CE) from 0 to 140 eV with a step size of 5 eV) in accordance with an embodiment of the present invention.
Figure 2B:
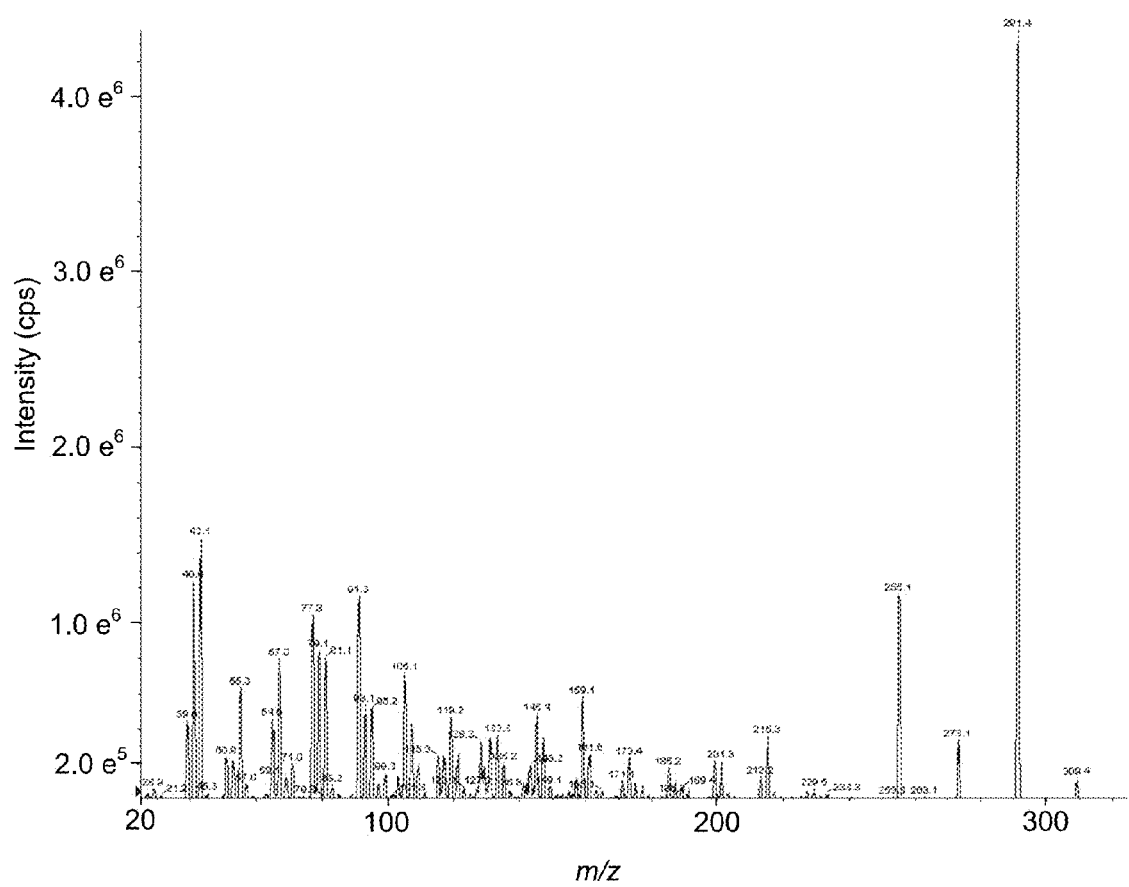

Neutral steroids, including 5α-dihydrotestosterone (DHT), are generally not good analytes for liquid chromatography-tandem mass spectrometry (LC-MS/MS) by atmospheric pressure ionization (API), due to ionization difficulty. Additionally, 5α-reduced steroids such as DHT show extremely poor response in all API methods, including Electrospray ionization (ESI), atmospheric pressure chemical ionization (APCI) and atmospheric pressure photoionization (APPI) due to low proton affinity. Testosterone (T) with conjugated 3-oxo-4-ene structure (FIG. 1) shows relatively high response in the positive ESI because the conjugated double bonds delocalize the charge of and stabilize the protonated molecules. For the same reason, T produces characteristic A-ring product ions (m/z 97 and 109) in MS/MS that are specific and of high abundance (FIG. 2). Unlike T and because of lack of 4-ene, DHT is neither ionized well nor produces specific fragment ions of high abundance. Most of developed methods for DHT without derivatization use fragment ions due to water loss (m/z 255 and 271) from the protonated molecular ions (FIG. 2), and thus lack sensitivity and specificity for measuring DHT at low pg/mL levels, especially in women and children.

To improve these limitations, various derivatization methods have been proposed to increase the ionization efficiency and method specificity. However, DHT has only one hydroxyl group and one ketone group that can be utilized. Derivatizing reagents targeting either one of the functional groups include acyl halide and carboxyl anhydride for the hydroxyl group and hydrazine and hydroxylamine for the ketone group. Several important factors for a high quality method include sample clean-up procedure, reaction conditions and post-derivatization treatment procedure. Derivatization of T or DHT with general hydroxylamines can include formation of geometric syn- and anti-isomers originating from imine-moiety that can result in problems in LC separation. The present disclosure uses hydroxylamines that provide rapid reaction, can be used under mild conditions, and preferably provide no post-derivatization pretreatment, thereby providing a simple method to achieve high throughput.

Figure 3A:
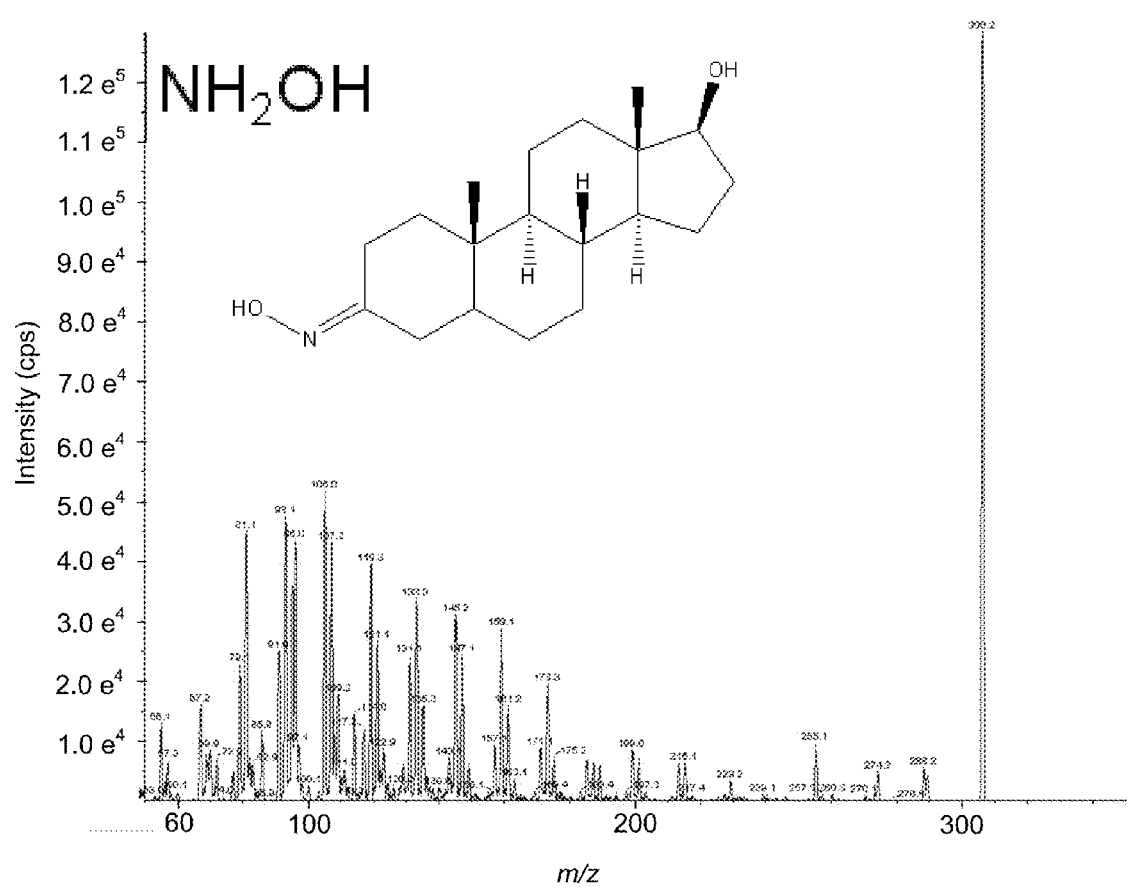
FIGS. 3A-B show MS/MS spectra of DHT oximes, (A) hydroxylamine, m/z 304 and (B) O-tert-butyl hydroxylamine, m/z 362 (the spectra was acquired by ramping collisional energy (CE) from 0 to 140 ev with a step size of 5 eV) in accordance with another embodiment of the present invention.
Figure 3B:
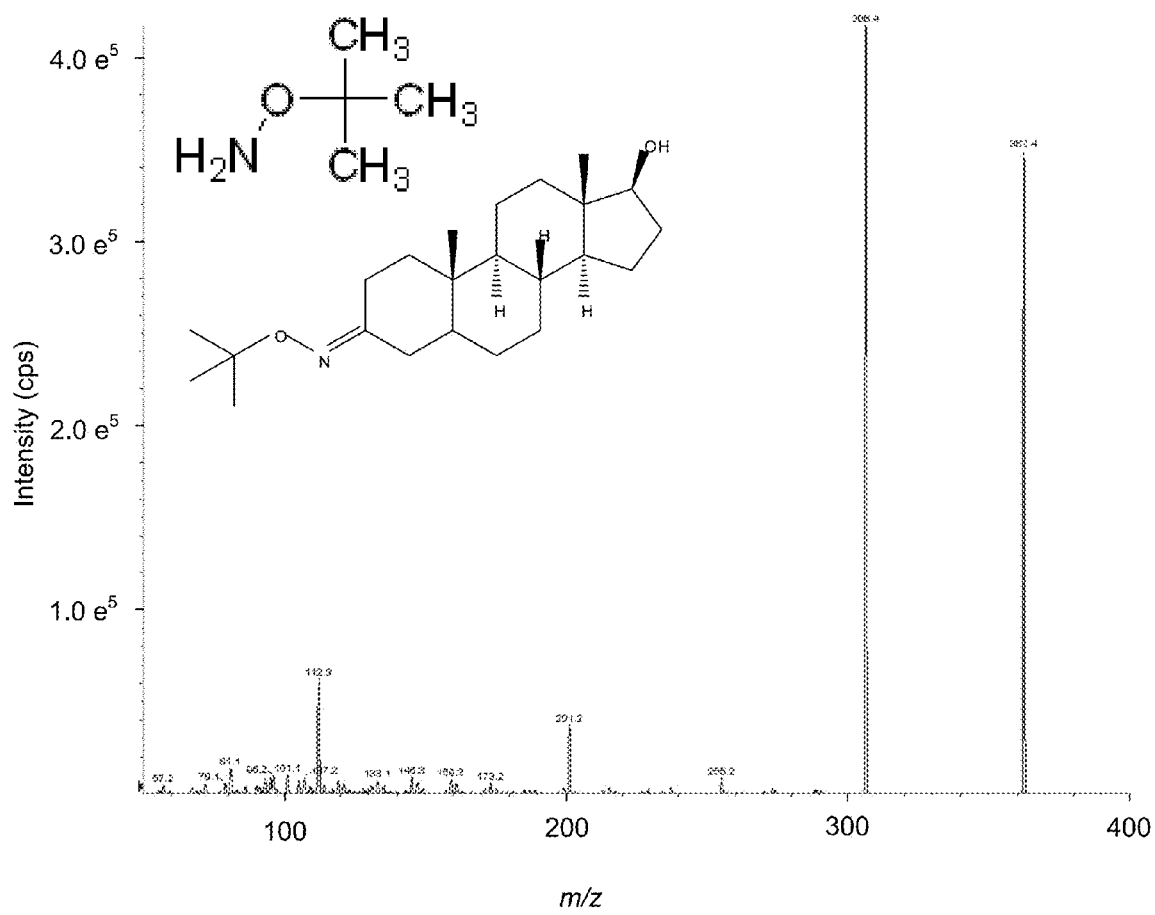

As such, the present methods use hydroxylamines to derivatize carbonyl group-containing compounds, including ketosteroids providing the above benefits previously unachieved. The MS/MS spectrum of DHT derivative by hydroxylamine (FIG. 3) does not show any specific fragment ions of high abundance. The many non-specific fragment ions are produced from breaking the rigid ring structure of high internal energy, just as underivatized DHT. The fragment ions due to water loss for DHT oxime are even lower than that from underivatized DHT. However, greatly improved ionization and fragmentation are obtained with DHT oxime by O-tert-butyl-hydroxylamine (FIG. 3). There is only one intensive fragment ion (m/z 362 to 306) believed to be from neutral loss of the O-tert-butyl moiety. Such may not be ideal due to lack of specificity and also the need of a secondary transition for confirmation purpose; however, it is recognized that any derivatization method of DHT analysis by LC-MS/MS shares this same problem (or fragment ions from only the derivatizing reagent) and necessitates sufficient LC separation to secure method specificity. The present derivatization does improve specificity by not reacting with some isobaric steroids that could potentially interfere with DHT, such as androstenediols that lack a ketone group.

Figure 4:
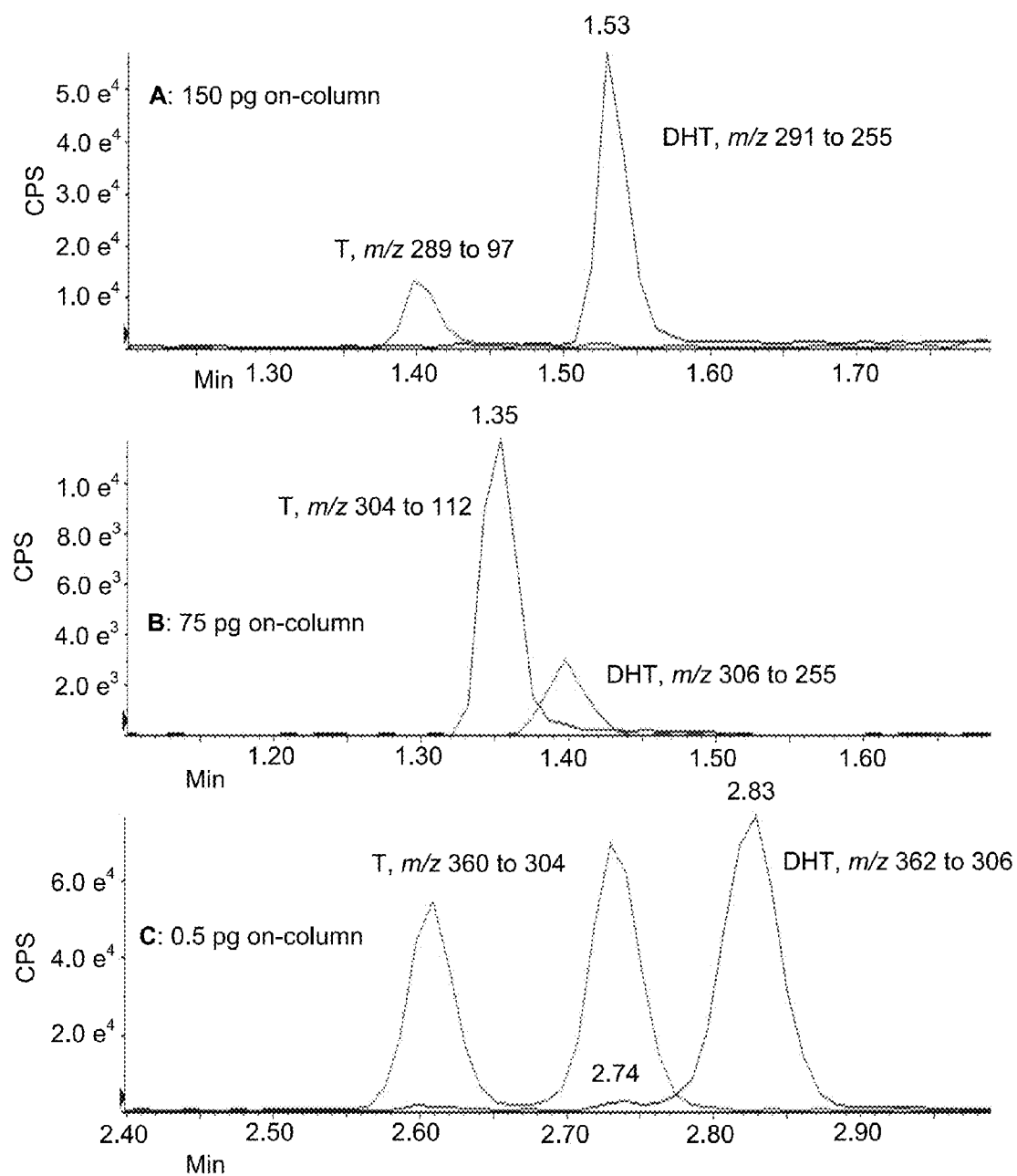
FIGS. 4A-C show chromatograms of T and DHT without derivatization (A) and derivatized with hydroxylamine (B) and O-tert-butyl hydroxylamine (C) in accordance with an embodiment of the present invention.

The derivatization performances are studied by analyzing standards without derivatization and with derivatization by hydroxylamine and O-tert-butyl hydroxylamine, in both selected ion monitoring (SIM) and multiple reaction monitoring (MRM) modes. The protonated molecule ions and the most abundant MRM transitions are used. The results are shown in Table 1 for DHT and FIG. 4 for both T and DHT.

TABLE 1

DHT sensitivity improvement by derivatization with hydroxylamine and O-tert-butyl hydroxylamine.

|  | m/z | m/z | Quantity[1] | Peak Area #1 | #2 | #3 | Mean | Fold[2] |
|---|---|---|---|---|---|---|---|---|
| MRM | | | | | | | | |
| 1* | 362.3 | 306.2 | 0.5 | 2.21E+05 | 2.10E+05 | 2.09E+05 | 2.13E+05 | 1237.9 |
| 2 | 306.2 | 255.2 | 75 | 5.66E+04 | 5.73E+04 | 6.27E+04 | 5.89E+04 | 2.3 |
| 3 | 291.2 | 255.1 | 150 | 5.33E+04 | 5.71E+04 | 4.47E+04 | 5.17E+04 | 1.0 |
| SIM | | | | | | | | |
| 1 | 362.3 | | 7.5 | 4.86E+06 | 4.79E+06 | 4.81E+06 | 4.82E+06 | 214.7 |
| 2 | 306.2 | | 75 | 2.73E+06 | 4.54E+06 | 4.47E+06 | 3.91E+06 | 17.4 |
| 3 | 291.2 | | 150 | 4.34E+05 | 4.46E+05 | 4.67E+05 | 4.49E+05 | 1.0 |

*1. No derivatization; 2. hydroxylamine; 3. O-tert-butyl hydroxylamine.
[1]Mass amount injected on column (pg).
[2]Fold, improvement in peak area, normalized to without derivatization.
MRM, multiple reaction monitoring.
SIM, selected ion monitoring.

The chromatograms are acquired under the same LC conditions as described below. The ionization efficiency and fragmentation efficiency are both greatly improved, resulting in >200 folds improvement in SIM and >1200 folds improvement in MRM for DHT by O-tert-butyl hydroxylamine, while MRM only improved by 2 folds despite 17 folds improvement in SIM due to inefficient fragmentation with hydroxylamine. With O-tert-butyl hydroxylamine, the ionization efficiency is improved by increased proton affinity and also efficient desolvation due to elution with high content of organic solvent in the mobile phase because of increased hydrophobicity that leads to much longer retention time as apparent in FIG. 4C; the efficient fragmentation further magnifies the overall performance. With hydroxylamine, the hydrophobicity of the DHT oxime is actually lower than DHT as indicated by shorter retention time in FIG. 4B, thus less efficient desolvation.

Figure 5A:
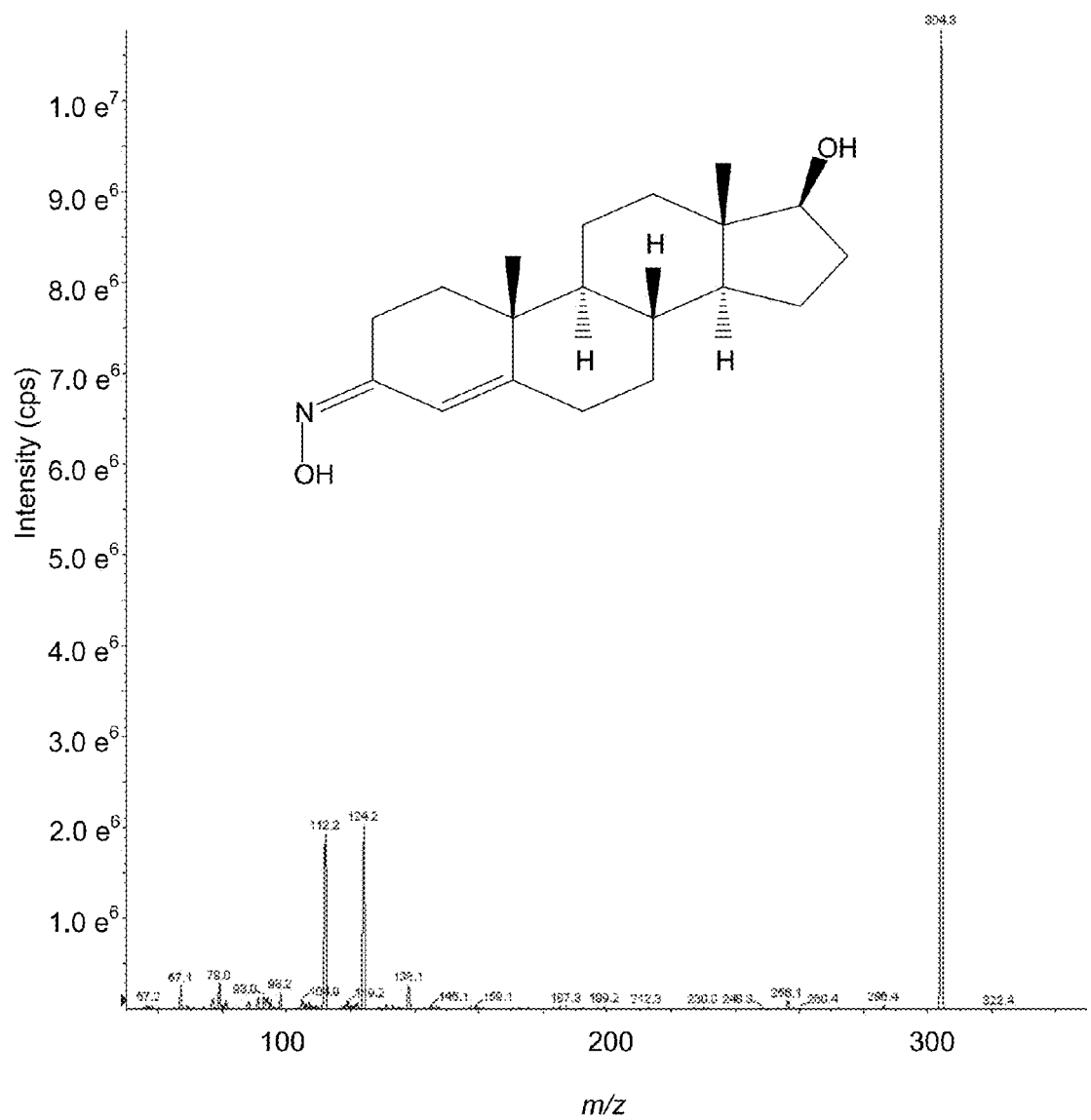
FIGS. 5A-B show MS/MS spectra of T oximes, (A) hydroxylamine, m/z 304 and (B) O-tert-butyl hydroxylamine, m/z 362 (the spectra was acquired by ramping collisional energy (CE) from 0 to 140 ev with a step size of 5 eV) in accordance with an embodiment of the present invention.
Figure 5B:
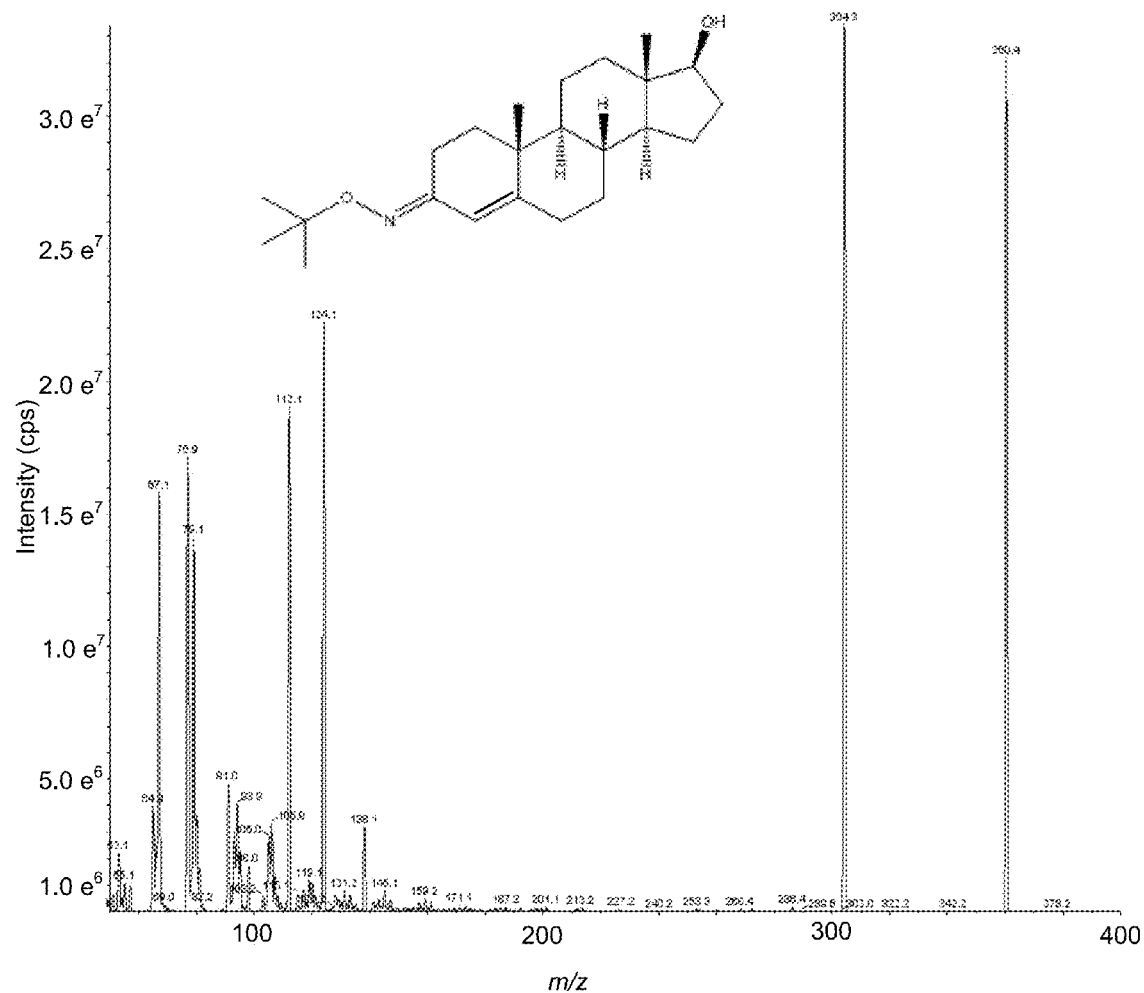

The oxime derivatives of T by both hydroxylamine and O-tert-butyl hydroxylamine produce specific fragments characteristic of 3-oxo-4-ene A ring as unmodified T while the T oxime derivative by O-tert-butyl hydroxylamine also produce high intensity fragment ions (m/z 360 to 304) by neural loss of tert-butyl group like DHT (FIG. 5). Apparent in FIG. 4, both T oximes greatly improved the overall sensitivity for T. Notably, the derivatization performance of T by O-tert-butyl hydroxylamine is at least as good as DHT.

As mentioned earlier, geometric cis-trans (E)-(Z) isomers can be formed with derivatization by hydroxylamines from the imine-moiety (FIG. 1) for both T and DHT. Both DHT oxime derivatives elute as a single chromatographic peak with good peak shape under the LC conditions described in the paper (FIGS. 4B and 4C). However, T oxime with hydroxylamine elute as single chromatographic peak while T oxime with O-tert-butyl hydroxylamine result in two chromatographic peaks completely baseline resolved. Extensive efforts (LC stationary phase, organic solvent, pH, additive) were made to merge the two T oxime peaks and separate T from DHT without success, although other different T oximes have been reported with single chromatographic peaks. While not intending to be bound by any particular theory, it is believed that 4-ene in the A ring of T makes it more rigid structure compared to DHT manifesting as steric effect in chromatographic separation. It is also believed that the large O-tert-butyl group plays an important role in terms of chromatographically separating the E- and Z-isomers.

Because of the great sensitivity improvement achieved by derivatizing T with O-tert-butylhydroxyamine, it is possible to achieve excellent sensitivity by quantifying either one oxime isomer/chromatographic peak with the use of a stable isotope labeled internal standard. Furthermore, it is possible to use the peak area ratio of the E- and Z-isomers for the purpose of identity confirmation basing on that the ratio is analytically reproducible in the same run (CV<15%), just as two MRM transitions are recommended.

Standard Addition Study

Figure 6A:
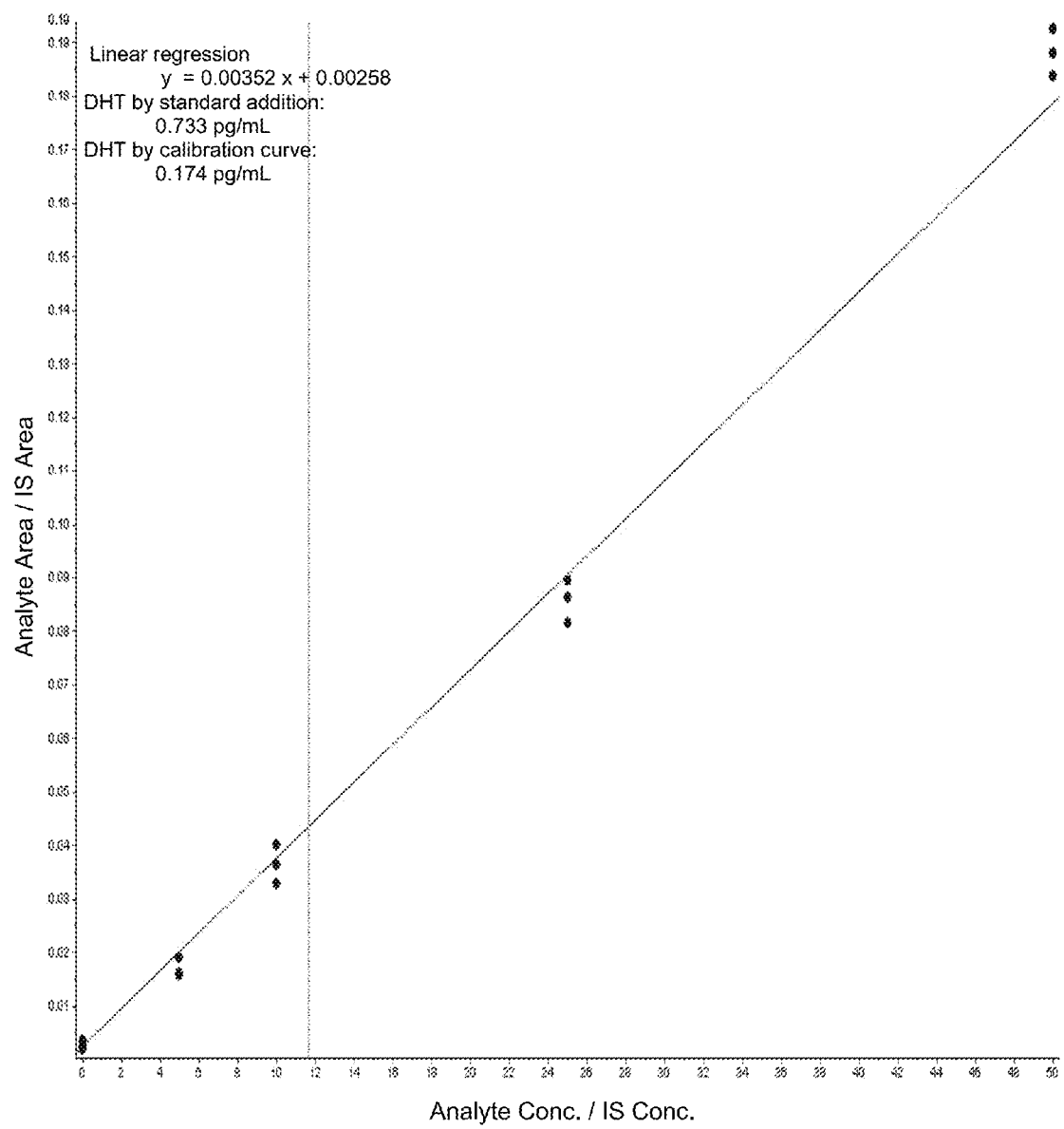
FIGS. 6A-B show linear regressions for a standard addition study into (A) a negative serum and (B) a positive serum in accordance with an embodiment of the present invention.
Figure 6B:
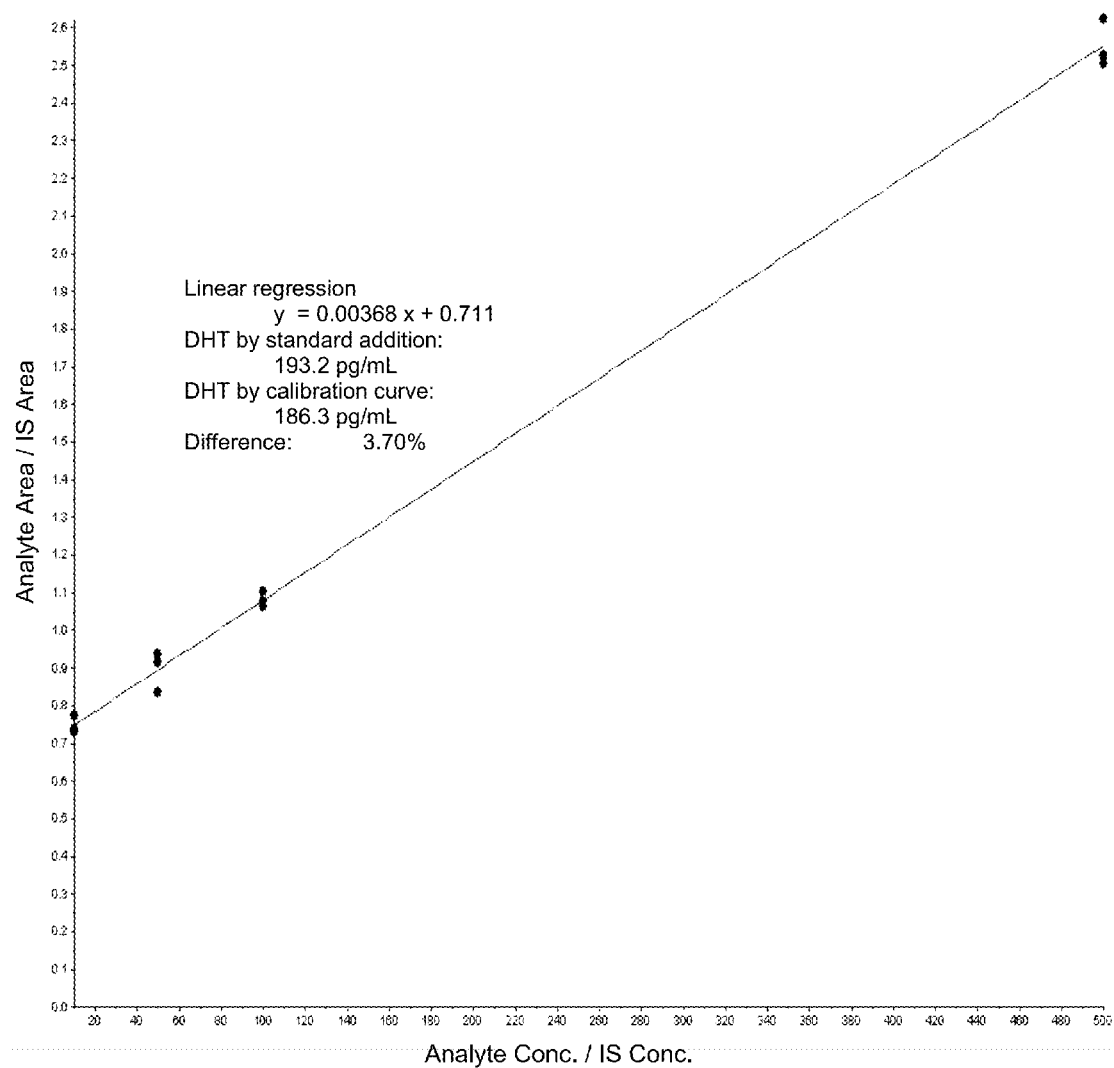

The standard addition study is used to dismiss concerns about the method accuracy since the calibration curve is prepared by freshly spiking standard solution into phosphate buffered saline (PBS) that is different from serum matrix in incurred specimens. Standard solution is freshly spiked at 0, 5, 10, 25 and 50 pg/mL into patient serum containing endogenous DHT, in triplicate at each concentration level. The analyte/IS peak area ratios are plotted against the spiked concentrations and linear regression is performed. The DHT concentration is determined by calculating the absolute intercept with the x-axis. The results obtained this way are compared to results by the calibration curve in the validated method as described. FIG. 6 shows two standard addition studies into (A) a negative serum and (B) a positive serum. The excellent agreement between the results shows that the validated method using PBS as the surrogate matrix for calibrators is accurate for DHT determination in serum. The method accuracy is further supported by method comparison.

Example 2—DHT Measurement Study for Women and Children

Background: Measurement of 5α-dihydrotestosterone (DHT) levels in circulation is important for assessing various pathophysiological conditions. The present example provides a liquid chromatography-tandem mass spectrometry (LC-MSMS) method for women and children.

Methods: Serum aliquots of 100 μL are spiked with internal standard and extracted with methyl tert-butyl ether. The extract is derivatized with tert-butyl-hydroxylamine and analyzed by LC-MS/MS using two-dimensional chromatography with a 4 min run time.

Results: DHT are determined with a lower limit of quantification of 2.5 pg/mL. The method correlated with one radioimmunoassay and one LC-MS/MS method. DHT levels increase for both girls and boys of age from 7 to 17 years trailing the trend of testosterone (T). Concentration levels characteristic of puberty/adults are achieved in girls at Tanner Stage (TS) 3 or age of 13 years and in boys at TS 4-5 or age of 15 years. The DHT/T ratio in boys from 15 to 17 year of age (mean±SD, 6.8%±0.3%) is similar to that reported for male adults. Reference intervals of both genders were established for adults and children of ages from 7 to 17 years (by age, TS and menarche status).

The present example provides for a simple rapid method for highly sensitive quantification of DHT in serum by LC-MS/MS. The method has adequate sensitivity and specificity for all age groups for both genders. Additionally, the present method can be used for age and gender specific reference intervals for children of age from 7 to 17 years.

Non-standard Abbreviations: DHT, 5α-dihydrotestosterone; T, testosterone; RIA, radioimmunoassay; $1^{st}$, $2^{nd}$, 2-D, dimensional; LC-MSMS, liquid chromatography-tandem mass spectrometry; SIM, selected ion monitoring; MRM, multiple reaction monitoring; RT, room temperature; IS, internal standard; PBS, phosphate buffered saline; LLOQ, lower limit of quantitation; ULOQ, upper limit of quantitation; MTBE, methyl tert-butyl ether; TS, Tanner stage.

Androgens play important roles in developmental and reproductive functions of both males and females. 5α-dihydrotestosterone (DHT) is the most potent androgen and is 3-10 times more potent than testosterone (T). It is well known that DHT plays critical roles in virilization including formation of the male external genitalia during embryonic life, and most aspects of pubertal onset and sexual maturation. Although DHT is produced by several organs including gonads, adrenal, prostate, and peripheral tissues through different biosynthetic pathways, DHT in circulation is primarily a peripheral product of T conversion.

Measurement of circulating DHT levels is useful for assessing patients with ambiguous genitalia, hirsutism, 5α-reductase deficiency, during treatments of prostate diseases and hypogonadism. However, the DHT levels in circulation are less than 10% of T and accurate DHT quantification is especially difficult for low concentration levels in women and children. To this aim, liquid chromatography-tandem mass spectrometry (LC-MSMS) has become the method of choice to measure DHT in serum for clinical applications, because of its high sensitivity and specificity.

LC-MSMS methods have been developed to quantify DHT with or without derivatization. However, the prior procedures have the following limitations: a large sample volume is required; lengthy and labor intensive sample preparation is necessary, including post derivatization treatment procedure; the sensitivity and specificity are insufficient for low concentration levels; and long run time deems high throughput impossible. Only a few methods obtained pg/mL sensitivity despite time consuming clean-up procedure and long run time. More importantly, most of the developed methods are not fully validated for clinical applications.

The present method provides a simple high-throughput method for highly sensitive quantification of DHT by LC-MS/MS, suitable for routine clinical laboratory use and with adequate sensitivity and specificity for women and children at low pg/mL levels. Further, pediatric and adult reference intervals for both male and female are established.

Standards and Reagents

DHT and deuterium-labeled DHT-$d_3$ used as internal standard (IS) are purchased from Sigma (St. Louis, Mo.) and Cerilliant (Round Rock, Tex.). The DHT impurity in DHT-$d_3$ is found to be insignificant. HPLC-grade water, methanol, methyl t-butyl ether (MTBE) and acetonitrile are obtained from VWR (West Chester, Pa.). All other reagents including O-tert-butyl hydroxylamine are purchased from Sigma and were of the highest purity commercially available. Stock standard solutions are prepared in acetonitrile at concentration of 1 mg/mL. A working standard solution is prepared in acetonitrile at concentration of 100 pg/mL. A working IS solution is prepared in acetonitrile at a concentration of 1000 pg/mL. Calibrators are prepared freshly in every run in 100 µL phosphate buffered saline (PBS) at concentrations of 0, 5, 10, 50 and 100 pg/mL. All studies with specimens from human subjects are approved by the Institutional Review Board of the University of Utah.

Sample Preparation

Aliquots (100 µL) of standards, controls, or patient serum are transferred into glass tubes. To each tube is added 10 µL of IS working solution and 300 µL water. The samples are extracted with 2 mL of MTBE and the organic phase is evaporated under nitrogen at 37° C. The residue is re-dissolved in 200 µL of water and methanol (6:4 by volume) containing 2% (g/ml) O-tert-butyl hydroxylamine used for derivatization (FIGS. 1B and 1D). After shaking gently for 10 min at room temperature (RT), the derivatized extract is transferred to 96-well plate and 50 µL is injected for analysis.

LC-MS/MS Method

The instrument consists of an API 5000 triple-quadrupole mass spectrometer with a TurboV™ ion source from AB/Sciex (Foster City, Calif.), two 1200SL binary pumps and one column oven from Agilent (Santa Clara, Calif.), a HTC PAL autosampler from Leap Technologies (Carrboro, N.C.) equipped with a fast wash station, and a 6-port switching valve from Valco (Huston, Tex.). The 2 dimensional (2D) LC-MSMS setup includes a valve position 1, where the sample is loaded onto the extraction column and the first stage of separation is applied, and a valve position 2, where the sample is transferred to the analytical column and the second stage of separation is applied.

A short guard column (Zorbax Eclipes XDB-CN, 12.5× 2.1 mm, 5 µm, Agilent) is used for the $1^{st}$ dimensional ($1^{st}$ D) LC separation at RT with 10 mM formic acid in water (A) and methanol (B) as mobile phase at a flow rate of 2 mL/min and a C8 column (Luna C8(2), 3 µm, 100 Å, 100×2 mm, Phenomenex) for the $2^{nd}$ dimensional ($2^{nd}$ D) LC separation at 45° C. with 10 mM formic acid in water (A) and acetonitrile (B) as mobile phase at a flow rate of 0.75 mL/min. The solvent gradient for $1^{st}$ D is as follows: 40% B at 0.0 min, linear ramp to 85% B in 1.0 min, linear ramp to 95% B in 0.1 min and hold for 1.5 min, linear ramp to 40% B in 0.1 min and hold for 1.3 mM. The solvent gradient for $2^{nd}$ D is as follows: 45% B for 0.7 min, linear ramp to 75% B in 0.3 min, linear ramp to 80% B in 2.0 min, linear ramp to 95% B in 0.1 mM and hold for 0.9 min. The 6-port valve is switched at 0.5 and 0.7 min to put the $1^{st}$ D column in serial connection before the $2^{nd}$ D column for 0.2 min to elute the analyte to the $2^{nd}$ D column.

The MS instrument is operated in positive-ion MRM mode with quadrupole Q1 and Q3 both at unit resolution. The other settings are optimized for maximum signal intensity (CAD 8, CUR 35, GS1 85, GS2 60, IS 4500, TEMP 600, DP 140, EP 5 and CXP 20). Two MRM transitions are monitored with m/z 362 to 306 Da for DHT and m/z 365 to 309 Da for DHT-$d_3$ respectively while the same precursor/ product mass transition for either DHT or DHT-$d_3$ is acquired using different collision energies (CE 35 for quantitation and 45 specificity assessment). All data are acquired and processed with Analyst™ 1.4.2 software (AB/Sciex). A quantitative calibration is performed with every batch of samples.

Assay Performance Characteristics

Performance parameters including accuracy, imprecision, linearity, lower limit of quantitation (LLOQ), upper limit of quantitation (ULOQ), specimen stability, potential interference and ion suppression is evaluated according to the CLSI guidelines. Method accuracy is studied by both standard addition and method comparison. In standard addition study, standard solution is freshly spiked at 0, 5, 10, 25 and 50 pg/mL into patient serum containing endogenous DHT, in triplicate at each concentration level. The results obtained by standard addition method and by calibration curve are compared. The method is compared with a LC-MS/MS method (n=30, Harbor-UCLA Medical Center) and a radioimmunoassay (RIA) method (n=48, Esoterix). Samples used are de-identified patient serums submitted for routine clinical testing. Prior to testing by any method, all samples are stored or transported at or below −20° C. The method recovery is determined by analyzing patient samples before and after spiking with standard solution. The observed differences are compared to the spiked concentrations.

Imprecision is evaluated by analyzing six serum pools with a large concentration range. The serum pools are prepared, aliquoted into microcentrifuge tubes, and stored frozen at −20° C. before analysis. One aliquot of each serum pool is analyzed in six replicate in one run per day over a five-day period.

The linearity was first evaluated with freshly prepared samples by spiking PBS with standards at concentration levels of (0, 2.5, 5, 10, 25, 50, 100, 250, 500, 1000, 2500, 5000 and 10000 pg/mL) in three separate runs. The LLOQ and ULOQ are then established by analyzing spiked PBS at lower (1, 2.5 and 5 pg/mL) and higher (1000, 2500 and 5000 pg/mL) ends of linearity in triplicate in each run with three separate runs on three different days. A criterion of maintaining inaccuracy within ±15%, imprecision (CV)<15% and a branching ratio of two mass transitions within ±30% is used to determine LLOQ and ULOQ, and to assess the assay specificity.

Stability under different storage conditions is evaluated as follows. Aliquots of human plasma sample are stored at RT, refrigerated (4° C.), and in a freezer (−20° C.). The samples are transferred into a −70° C. freezer after 1, 3, 7, 14, 21, and 28 days of storage and analyzed in a single batch.

The potential interferences are investigated by examining chromatograms and quantitative results of patient samples acquired with two transitions (n>2000). A branching ratio of the two transitions outside of ±30% limits, broadening of the chromatographic peaks, split peaks or an increase in the background, are interpreted as potential interference. Ion suppression is evaluated using a post-column infusion method with patient samples of DHT <20 pg/mL. A standard solution (10 ng/mL, derivatized) is introduced into the flow path after the analytical column, resulting in an elevated baseline for every transition. A decrease in the intensity of the baseline is considered evidence of ion suppression.

Reference Intervals

Serum samples for reference interval study are collected from apparently healthy volunteers after obtaining informed consent. Serum is separated from red blood cells within 1 hour after collection and the samples were stored at −70° C. prior to analysis. The participants are not taking prescription medications; women on oral contraceptives or hormone replacement therapy are excluded from the study. Blood from adult participants is drawn between 8-10 am; over 90% of participants are of Caucasian descent. The mean (median) ages of the adult volunteers are 34.6 (33.1) and 32.5 (29.7) years for women (n=123) and men (n=152) of age from 18 to 60 years, respectively. Samples from children of ages 7 through 17 years (n=1604) are collected after obtaining parental permission in a research setting. Children enrolled in the study are not taking prescription medications and have no known medical conditions or disorders. In the present study, The Tanner stage (TS) in boys is determined by a male physician assistant and in girls by a female clinical study coordinator; both are trained by an endocrinologist.

Data Analysis

Statistical data analysis is performed with EP Evaluator (David G. Rohoads Associates, Kennett Square, Pa.) and Excel (Microsoft, Redmond, Wash.). Method comparison is analyzed by Deming regression and Bland-Altman plots are constructed with the percentage difference between the methods against the average concentration of the two methods. Reference intervals are determined using non-parametric method (central $95^{th}$ percentile). The single factor analysis of variance (ANOVA) with α=0.05 is used for stability study and to study differences between groups. Comparisons resulting in P<0.01 are considered statistically significant.

Results

Figure 8:
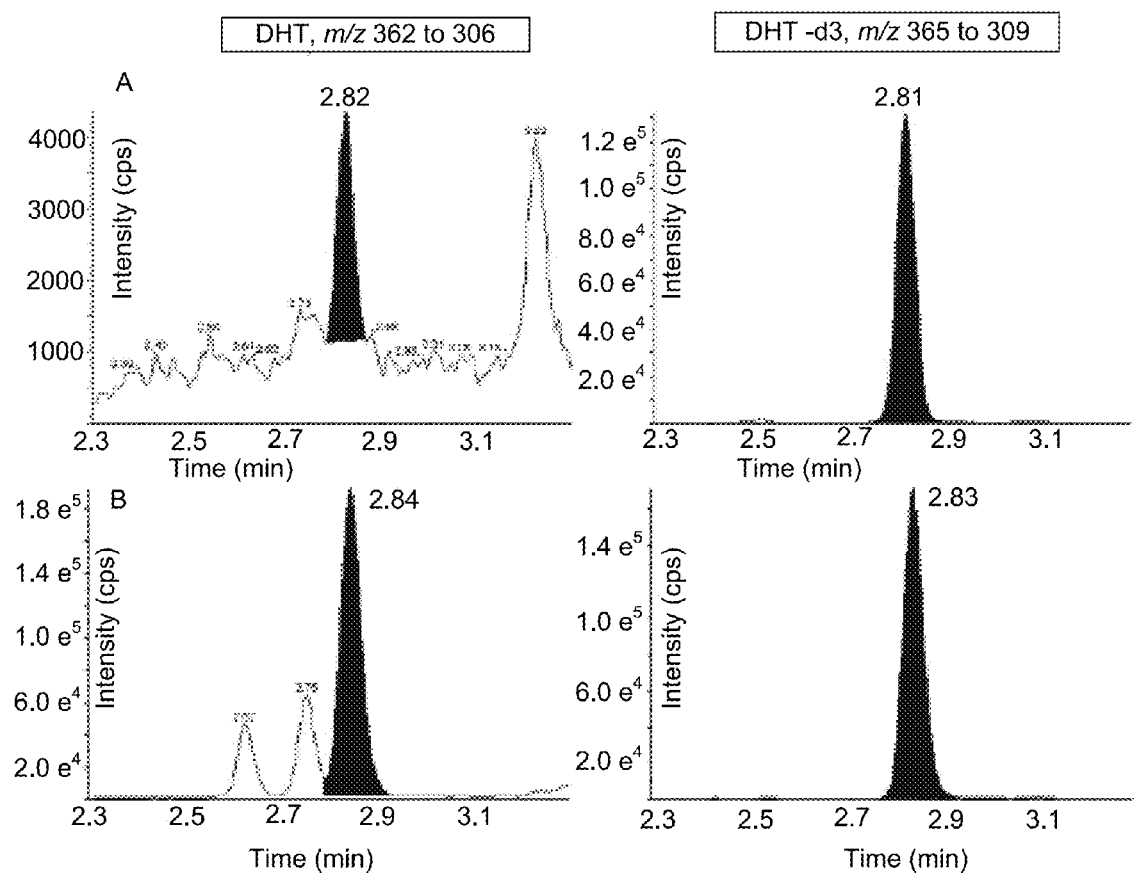
FIG. 8A-B shows chromatograms of (A) a girl of 7 year old with measured DHT of 2.5 pg/mL and (B) a boy of 16 year old with measured DHT of 200 pg/mL in accordance with an embodiment of the present invention.
Figure 9:
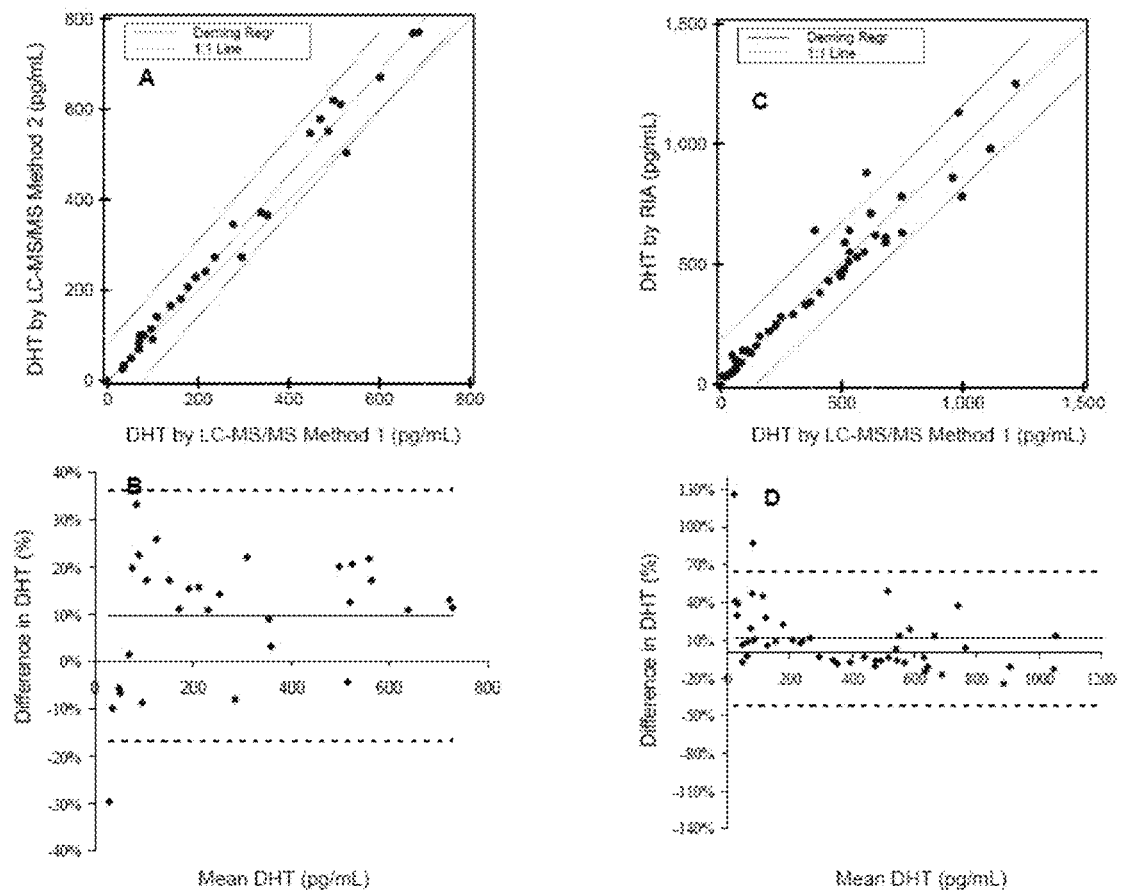
FIGS. 9A-D show scatter (A and C) and Bland-Altman plots (B and D) for method comparison in accordance with an embodiment of the invention.

The chromatograms of a girl of 7 year old with measured DHT of 2.5 pg/mL and a boy of 16 year old with measured DHT of 200 pg/mL are illustrated in FIG. 8. The results for standard addition studies are presented in the FIG. 6. Scatter and Bland-Altman plots for method comparison are illustrated in FIG. 9. The correlation between the described method (x) and a validated LC-MS/MS method (y, Harbor-UCLA Medical Center) is observed with y=1.14x−3.70, $S_{y/x}$=29.8, r=0.99, n=30. The correlation between the described method (x) and a RIA method (y, Esoterix) is observed with y=0.97 x+21.2, $S_{y/x}$=82.0, r=0.97, n=48.

The LLOQ and ULOQ are determined to be 2.5 pg/mL and 2500 pg/mL respectively using criteria of ±15% inaccuracy for single measurement and within-run mean against nominal concentrations, and CV<15% for within-run, between-run and total imprecision. Signal to noise ratio at LLOQ is greater than 20. With serum pools, the within-run, between-run, and total imprecision (CV %) are <6.7%, <6.5% and <7.6% respectively for DHT concentration ranging from 5 to 1000 pg/mL (Table 2).

TABLE 2

Method imprecision.

| Sample # | Mean DHT Conc. (pg/mL) | Between-run CV % | Within-run CV % | Total CV % |
|---|---|---|---|---|
| 1 | 5.2 | 3.90% | 6.50% | 7.60% |
| 2 | 27 | 5.00% | 3.80% | 6.30% |
| 3 | 39.8 | 2.70% | 3.40% | 4.30% |
| 4 | 193.1 | 6.70% | 3.40% | 7.50% |
| 5 | 545.4 | 2.40% | 2.20% | 3.30% |
| 6 | 1030.9 | 4.60% | 2.30% | 5.10% |

The CV obtained in LLOQ, ULOQ and linearity with spiked PBS (data not shown) is similar to that obtained in serum pools for imprecision study. Good stability is demonstrated for all conditions evaluated (RT, 4° C., and −20° C.) for up to 28 days. In reference to time 0, the DHT results at different time points range from 94.6% to 104.7% for all conditions. The P-values are >0.05 for single factor ANOVA for all conditions. Notably, the human plasma matrix used for the stability study is different from the targeted serum matrix. No significant difference in the recovery is observed between serum and EDTA plasma matrices. Processed specimen is stable at RT or refrigerated condition for at least 3 days.

No ion suppression is observed at the retention time of DHT. Potential interferences include isomeric steroids (etiocholanolone, epietiocholanolone, androsterone, epiandrosterone, 5β-DHT and androstenediols) and other steroids isotopic ions of which are isobars of DHT (e.g. T). Without intending to be bound by any particular theory, it is believed that all of them were chromatographically separated from DHT and those that don't have ketone moiety were not derivatized. No evidence of interference is observed for DHT and its IS in >2000 patient samples.

Reference intervals of DHT determined using nonparametric method (CLSI C28-A) for healthy children of 7 through 17 years and adults of both genders are summarized in Table 3 including different pediatric groups of age, Tanner stage and menarche status.

TABLE 3

Reference intervals of DHT in children and adults [determined using nonparametric method (CLSI C28-A)].

| | | Female | | | Male | |
|---|---|---|---|---|---|---|
| Age group | N | Lower limit | Upper limit | N | Lower limit | Upper limit |
| 7-9 | 219 | <2.5 | 42(31.2, 142) | 219 | <2.5 | 31.7(21.3, 47.4) |
| 10-11 | 146 | 3.1(<2.5, 5.4)* | 74.6(59.1, 160.5) | 145 | 2.7(<2.5, 3.6) | 280.5(97.1, >425) |
| 12-13 | 147 | 8.5(6.9, 11.3) | 130.3(94.9, 367) | 147 | 8.5(3.2, 14.8) | 546(397, 733.5) |
| 14-15 | 145 | 12.3(<7.5, 25.2) | 148.3(124, >175) | 148 | 46.1(8.8, 82.8) | 474.2(450, 502) |
| 16-17 | 141 | 23.4(<2.5, 28.4) | 197.6(174, >345) | 144 | 38.5(<2.5, 103) | 507.1(477, >809) |
| T1 | 311 | <2.5 | 64.7(51.0, 115.0) | 296 | <2.5 | 50.2(39, 93.7) |
| T2 | 133 | 5.5 (<5.3, 8.6) | 101(76.4, >108.5) | 135 | 3.9(<2.5, 6.4) | 393.8(221.5, >450) |
| T3 | 139 | 11.8(<7.5, 17.4) | 161.8(143, 211) | 145 | 15.2(<8.8, 31.6) | 589.5(450, >767) |
| T4/T5 | 216 | 19.5(<2.5, 24.4) | 191(155, 367) | 213 | 90.7(<2.5, 119) | 505.5(477, 854) |
| Pre-Menarche | 434 | <2.5 | 77.3(64.7, 112) | | | |
| Post Menarche | 334 | 14.6(10.5, 18.8) | 180.5(156.5, 211) | | | |
| Adult (18-60) | 120 | 24.5(<20.8, 29.6) | 208.4(177.5, >470) | 151 | 105.7(85, 122.5) | 718.6(632.5, 809) |

*95% confidence intervals

Figure 7:
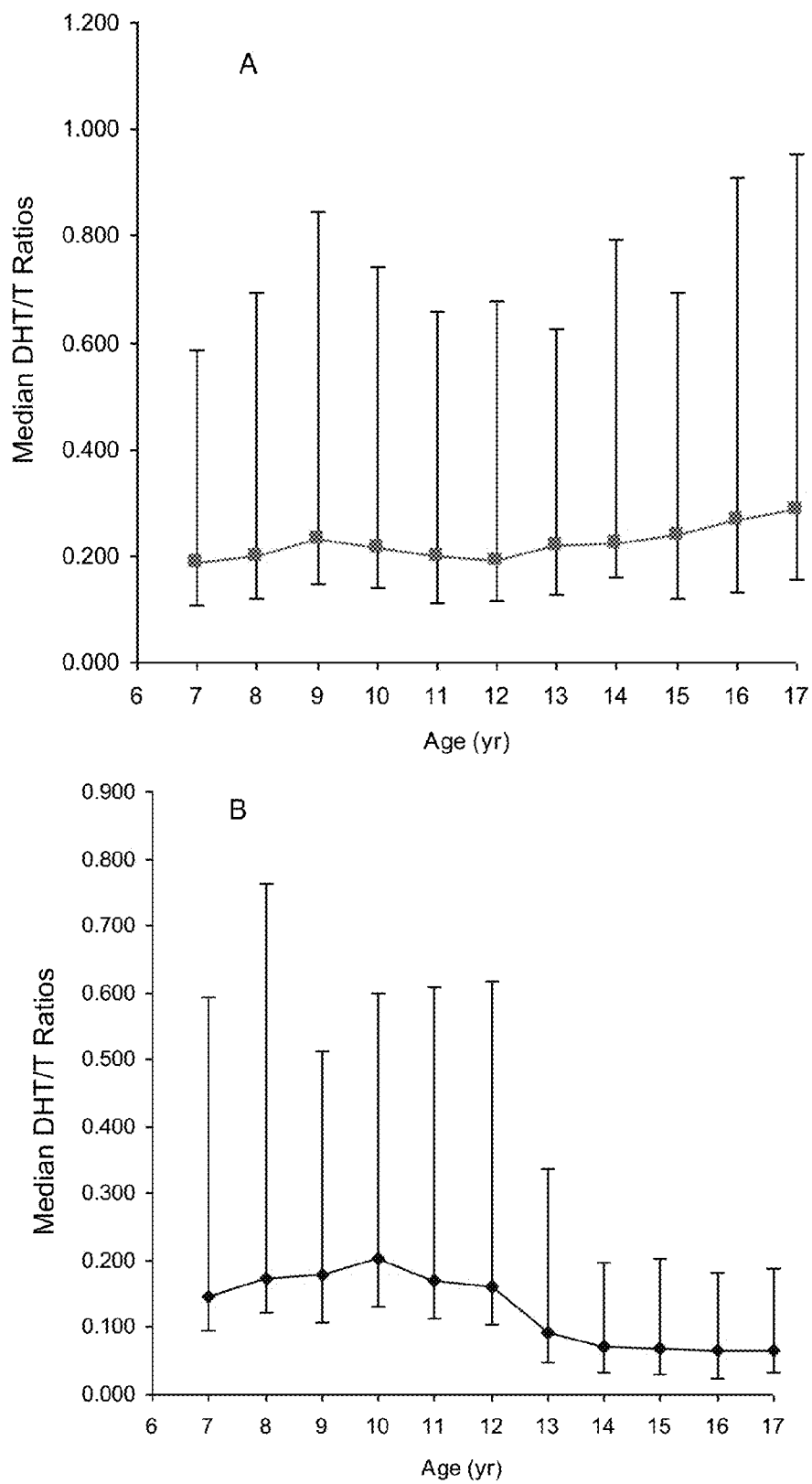
FIGS. 7A-B show median DHT/T ratios in samples from girls (A) or boys (B) of 7 through 17 years, with error bars representing the minimum and maximum ratios observed, in accordance with an embodiment of the present invention.
Figure 10:
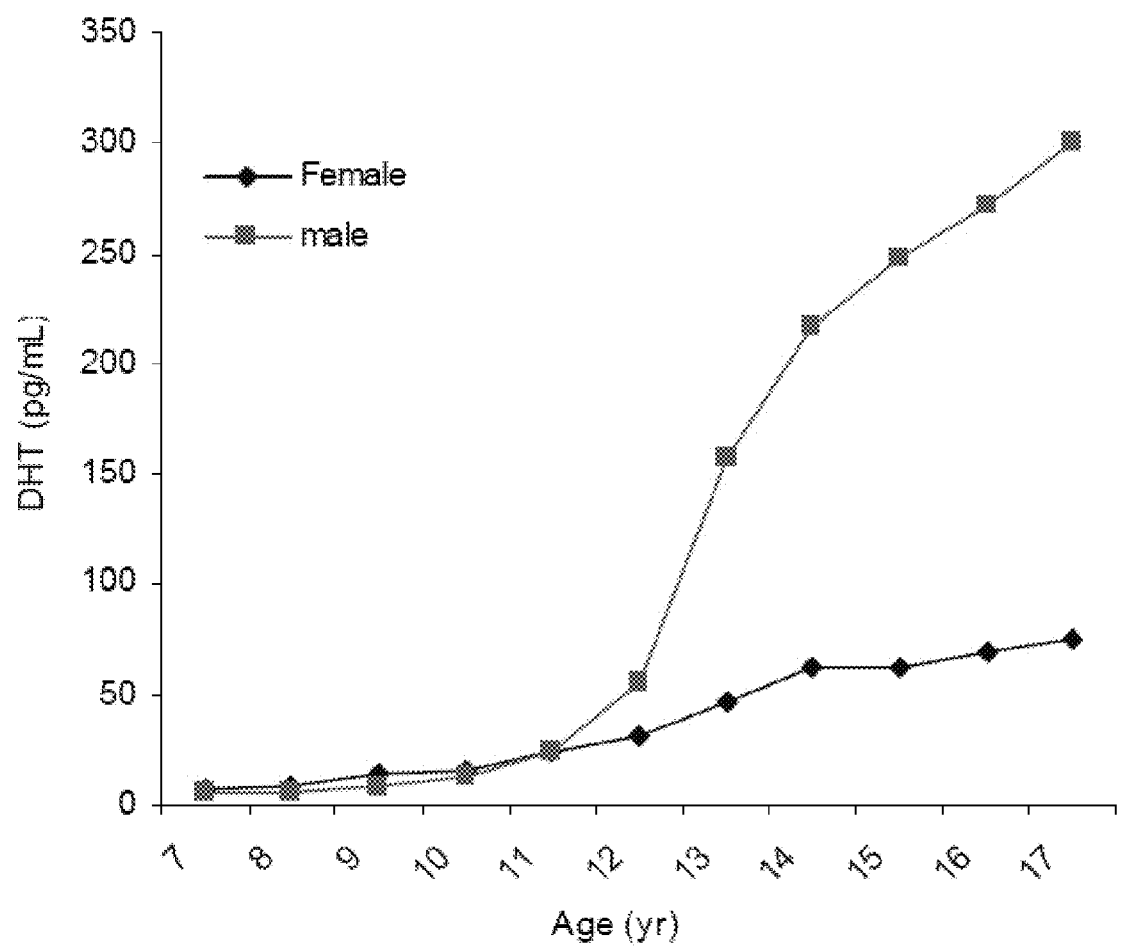
FIG. 10 shows a plot of median DHT concentrations of different ages and sexes in pediatric samples used to establish reference intervals in accordance with an embodiment of the present invention.
Figure 11:
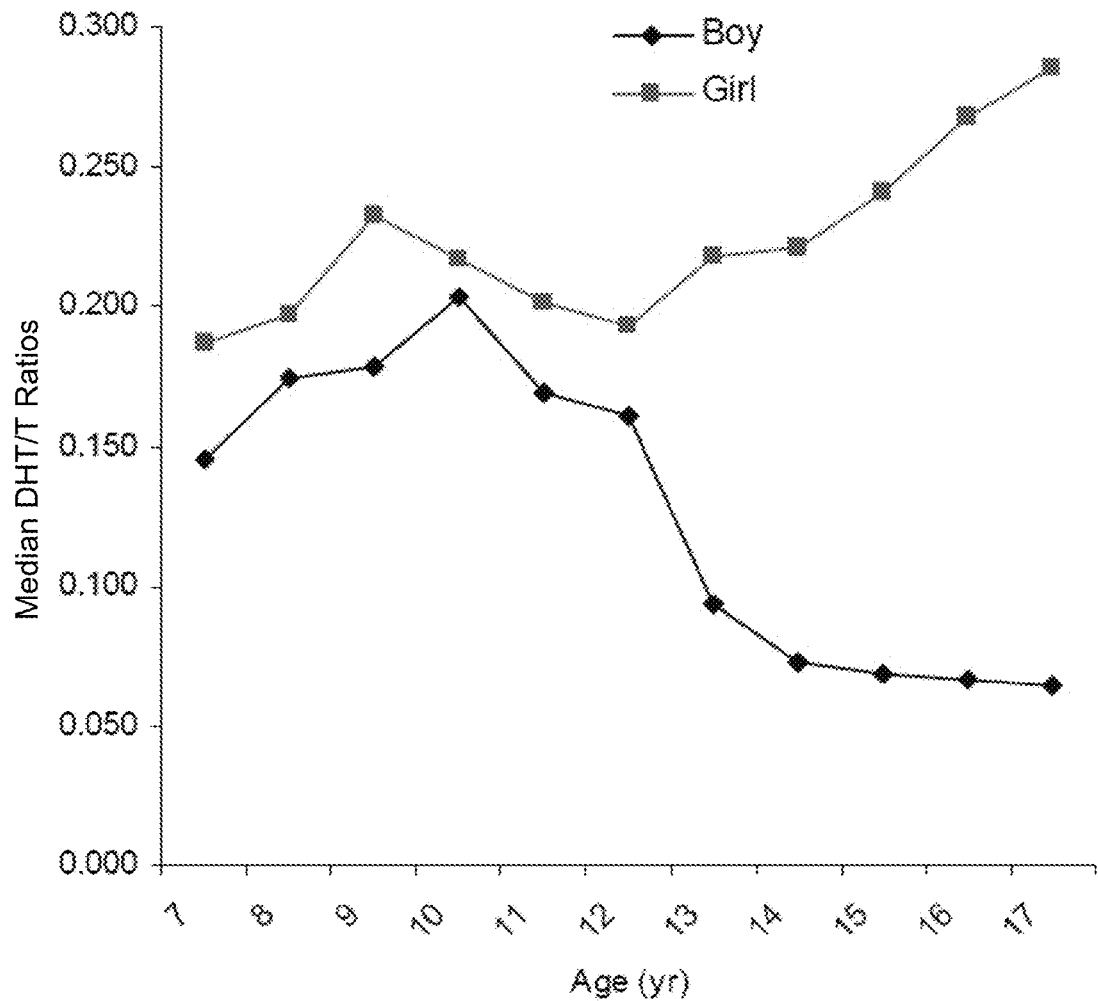
FIG. 11 shows a plot of the median DHT/T ratio of different ages and sexes in accordance with an embodiment of the present invention.

The median DHT concentrations of different ages and sexes in pediatric samples used to establish reference intervals are plotted in FIG. 10. P-values for comparisons across different age groups, tanner stages and pre-/post menarche as well as girls vs. boys for DHT in pediatric samples are presented in Table 4. The T concentrations in the same set of samples are also measured by another method and the median DHT/T ratio of different ages and sexes are plotted in FIG. 11 (see FIG. 7 that contains error bars representing the observed range).

TABLE 4

P-values of single factor ANOVA with α = 0.05 for DHT in pediatric samples across different age groups, tanner stages and pre-/post menarche as well as girls vs. boys.

| Age Group | P-Value Girls | P-Value Boys | Age Group | P-Value Girls vs. Boys | Tanner Stage | P-Value Girls | P-Value Boys |
|---|---|---|---|---|---|---|---|
| 7 | na | na | 7 | 0.158 | 1 | na | na |
| 8 | 0.017 | 0.224 | 8 | 0.007 | 2 | 0.000 | 0.000 |
| 9 | 0.002 | 0.005 | 9 | 0.004 | 3 | 0.000 | 0.000 |
| 10 | 0.199 | 0.000 | 10 | 0.987 | 4&5 | 0.089 | 0.000 |
| 11 | 0.003 | 0.001 | 11 | 0.037 | Pre vs. Post | 0.000 | |
| 12 | 0.017 | 0.000 | 12 | 0.000 | | | |
| 13 | 0.000 | 0.000 | 13 | 0.000 | | | |
| 14 | 0.113 | 0.004 | 14 | 0.000 | | | |
| 15 | 0.282 | 0.222 | 15 | 0.000 | | | |
| 16 | 0.036 | 0.460 | 16 | 0.000 | | | |
| 17 | 0.978 | 0.207 | 17 | 0.000 | | | | na, P-value not available as the starting group or the comparison series.
pre vs. post, pre-menarche vs. post menarche.

Procedure and Method

Different approaches for DHT analysis show greater sensitivity by derivatization compared to protonated molecular ions without derivatization using atmospheric pressure ionization. A number of derivatization reagents are tested to achieve the sensitivity needed for DHT, targeting either the carbonyl moiety or the hydroxyl moiety. The challenges with most derivatizing reagents are harsh reaction conditions, long incubation time and excess reagent needed for complete derivatization and necessity for removal before LC-MS/MS analysis. However, the present inventors have discovered that O-tert-butyl hydroxylamine can react quickly with keto-steroids under mild conditions, provide greatly enhanced sensitivity, and require no post-derivatization treatment procedure with 2D LC. The ionization efficiency and fragmentation efficiency are improved by >200 folds in selected ion monitoring (SIM) and >1200 folds in multiple reaction monitoring (MRM) mode for DHT (see Supplemental Data for more details).

As previously noted, there are two issues with derivatization by O-tert-butyl hydroxylamine. First, there is only one intensive fragment ion (m/z 362 to 306) resulting from neutral loss of the O-tert-butyl moiety. The same transition is acquired at two different CE to obtain two transitions required for confirmation purpose. Secondly, geometric cis-trans isomers can be formed from the imine-moiety (FIG. 1). Both geometric isomers of DHT oxime elute as a single chromatographic peak with good peak shape under the LC conditions described and similar was observed in. To secure the specificity, 2D-LC-MS/MS is utilized to provide sufficient chromatographic resolving power to separate potential interferences including isomeric steroids and other steroids that have heavy isobars as DHT (e.g. T). The best selectivity for chromatographic separation in this method is achieved with a propyl-cyano and a C8 phase in 2DLC. By combing the derivatization scheme and 2D-LC-MS/MS, the advantages of this method includes simple sample preparation procedure, high sensitivity, specificity and throughput compared to previously known methods.

Performance Evaluation

Method comparisons show good agreement with one LC-MS/MS and one RIA assay (FIG. 9). Despite the slopes obtained by Deming regression, the scatter plot compared to RIA (FIG. 9C) shows more scattering than when compared to a LC-MS/MS method (FIG. 9A), especially at high concentration levels, possibly resulting from antibody saturation and the resultant nonlinearity. The Bland-Altman plot compared to RIA (FIG. 9D) shows larger discrepancies over the concentration range studied, implying overall lower performance. Both Bland-Altman plots (FIGS. 9B and 9D) show large difference at low concentration levels, possibly attributing to assay sensitivity, and about +10% constant biases compared to the developed method that is possibly attributing to specificity. Both comparison methods are less sensitive than the developed LC-MS/MS method.

There is a concern for the method to use PBS as surrogate matrix for calibrators. However, the standard addition studies and method comparisons clearly proved the method accuracy. Provided that specificity can be secured by 2D-LC-MS/MS, there should be no problem to use simple surrogate matrix in calibrators for endogenous analytes since negative biological matrix is difficult to obtain.

The method is validated with a LLOQ of 2.5 pg/mL and a ULOQ of 2500 pg/mL for practical reason (to avoid excessive repeats). Since the method use only 100 μL serum and an injection volume of 50 μL out of 200 μL reconstitution volume, the LLOQ can be easily improved. However, the current LLOQ is sufficient for the clinical need as only 8.2% of pediatric specimens from age groups of 7 to 11 years are tested with DHT below the LLOQ. As shown in FIG. 8A, the chromatogram for a girl of 7 year old with DHT of 2.5 pg/mL is obtained with sufficient ion counts and signal to noise ratio.

The high performance of this method suggests that it is suitable for measurement of DHT in groups of populations with low endogenous concentrations. Because of a lack of sensitive and specific methods for DHT measurement, limited information on pediatric reference intervals has been previously reported. Therefore, the present method establishes reference intervals for DHT in children and adults.

Reference Intervals

Despite very low endogenous levels especially in prepubertal children, androgens play critical roles in developmental and reproductive functions in children of both sexes. Thus, age-specific reference intervals for androgens in children are important for pediatric endocrinology considering variable concentrations with gender and age. Available data on DHT levels in pediatric samples are scarce due to lack of assay with sufficient specificity and sensitivity, and are also controversial because of dependence on methodology.

For children of 7 to 17 years of age, DHT concentration levels are found to be dependent on age, gender, and TS. (Table 3). In both sexes, DHT levels increase with ages (FIG. 10) trailing the pattern of testosterone (data not shown) with the highest rate between 12 to 14 years of age, possibly due to gonad maturation. In boys, DHT levels are not significantly different for ages of 7 and 8 year, significantly different for every age group between 8 and 14 years of age, not significantly different for ages of 15 to 17 year (Table 4). In girls, DHT levels are significantly different for age groups of (7 and 8), (9 and 10), (11 and 12) and (13 to 17) year, more like a stepwise pattern. It is interesting to observe that DHT levels in girls are significantly higher than boys in age groups of 8 and 9 years. It is consistent with previous observations that puberty onset starts at 8 years of age for both sexes, boys reach puberty at 15 years of age and TS 4 or 5 while girls reach puberty at 13 years of age and TS 3. Between-gender differences and the differences in the trends for age-specific changes warrant age and gender-specific reference intervals (Table 3). It is reasonable to break into age groups by statistically significant difference. However, in order to satisfy the requirement of >120 subjects by non-parametric method u and for practical clinical use, the age groups are formed in a more traditional and arbitrary way (Table 3).

In girls, the median DHT/T ratio increases from 7 to 9, then decreases and reaches a nadir at 12, and increase again from 12 to 17 years of age (FIG. 11); the observed increase from age 12 to 17 year of age could be attributed to increased 5α-reductase activity due to growth of large organs (e.g. skin and liver). In boys, the median DHT/T ratio increases from 7 to 10, then decrease gradually before 12 and steeply from 12-14, and reach a plateau at 15-17 year of age. The median DHT/T ratio in boys of 7 to 12 years of age is similar to girls (>14.5%). The much lower DHT/T ratio in boys from 15 to 17 year of age (mean±SD, 6.8%±0.3%) is similar to that reported in normal male adults (9-11) and can be contributed to overwhelming high testosterone from gonad maturation and possible saturation of 5α-reductase.

In summary, the present disclosure provides a simple high throughput (4 min run time) method for highly sensitive (2.5 pg/mL with 100 μl) quantification of DHT in serum by 2DLC-MS/MS, suitable for routine clinical laboratory use. The method has adequate sensitivity and specificity to measure DHT levels for different age and gender groups, especially for women and children. The pediatric data support the need for high sensitivity DHT measurement (pg/mL level). Using this method, reference intervals for adult male and female were established, as well as age and gender specific pediatric reference intervals by age, Tanner stage and menarche status.

While the disclosure has been described with reference to certain preferred embodiments, those skilled in the art will appreciate that various modifications, changes, omissions, and substitutions can be made without departing from the spirit of the disclosure. It is intended, therefore, that the invention be limited only by the scope of the following provisional claims.

What is claimed is:

1. A method of increasing the sensitivity for detection of a ketosteroid by mass spectrometry can comprise derivatizing the ketosteroid with an O-substituted hydroxylamine thereby producing an oxime, resulting in enhanced sensitivity of detection by mass spectrometry as compared to the underivatized ketosteroid, wherein the O-substituted hydroxylamine is an O-alkyl-hydroxylamine having the structure as shown in Formula I:

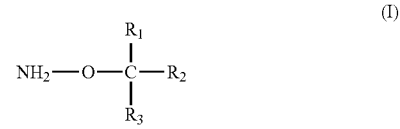

wherein $R_1$, $R_2$, and $R_3$, are, independently, linear or branched, substituted or unsubstituted, alkyl groups or hydrogen, and wherein at least two of $R_1$, $R_2$, and $R_3$ cannot be hydrogen, wherein detection of the ketosteroid is performed with a mass spectrometer operatively connected to a liquid chromatography separations module, and wherein the enhanced sensitivity of detection provides a lower limit of quantitation (LLOQ) for the ketosteroid of less than or equal to 100 pg/ml at an injection volume of 50 microliters.

2. The method of claim 1, wherein at least one of $R_1$, $R_2$, or $R_3$ is methyl.

3. The method of claim 1, wherein the ketosteroid is 5α-dihydrotestosterone or testosterone.

4. The method of claim 1, wherein derivatizing provides a greater than about 10 fold increase in ion signal.

5. The method of claim 1, wherein $R_1$, $R_2$, and $R_3$ of the O-alkyl-hydroxylamine are methyl.

6. A method for assaying a ketosteroid comprising derivatizing the ketosteroid for increased sensitivity of detection by mass spectrometry as compared to the underivatized ketosteroid by reacting the ketosteroid in a sample with an O-substituted hydroxylamine to produce an oxime and detecting the oxime by a mass spectrometry instrument, wherein the O-substituted hydroxylamine is an O-alkyl-hydroxylamine having the structure as shown in Formula I:

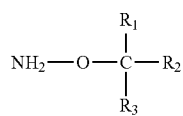

(I)

wherein $R_1$, $R_2$, and $R_3$, are, independently, linear or branched, substituted or unsubstituted, alkyl groups or hydrogen, and wherein at least two of $R_1$, $R_2$, and $R_3$ cannot be hydrogen, wherein detection of the ketosteroid is performed with a mass spectrometer operatively connected to a liquid chromatography separations module, and wherein the enhanced sensitivity of detection provides a lower limit of quantitation (LLOQ) for the ketosteroid of less than or equal to 100 pg/ml at an injection volume of 50 microliters.

7. The method of claim 6, wherein the mass spectrometry is done in multiple reaction monitoring (MRM) mode or in selected ion monitoring (SIM) mode.

8. The method of claim 6, wherein at least one of $R_1$, $R_2$, or $R_3$ is methyl.

9. The method of claim 6, wherein the ketosteroid is 5α-dihydrotestosterone or testosterone.

10. The method of claim 6, wherein $R_1$, $R_2$, and $R_3$ of the O-alkyl-hydroxylamine are methyl.

11. A method for assaying 5α-dihydrotestosterone or testosterone comprising derivatizing the 5α-dihydrotestosterone or testosterone for increased sensitivity of detection by mass spectrometry as compared to the underivatized 5α-dihydrotestosterone or testosterone by reacting the 5α-dihydrotestosterone or testosterone in a sample with an O-substituted hydroxylamine to produce an oxime, and detecting the oxime by a mass spectrometry instrument, wherein the O-substituted hydroxylamine is an O-alkyl-hydroxylamine having the structure as shown in Formula I:

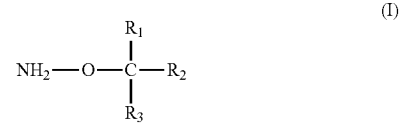

(I)

wherein $R_1$, $R_2$, and $R_3$, are, independently, linear or branched, substituted or unsubstituted, alkyl groups or hydrogen, and wherein at least two of $R_1$, $R_2$, and $R_3$ cannot be hydrogen, wherein detection of the 5α-dihydrotestosterone or testosterone is performed with a mass spectrometer operatively connected to a liquid chromatography separations module, and where the enhanced sensitivity of detection provides a lower limit of quantitation (LLOQ) for the 5α-dihydrotestosterone or testosterone of less than or equal to 100 pg/ml at an injection volume of 50 microliters.

12. The method of claim 11, wherein the mass spectrometry instrument is a liquid chromatography tandem mass spectrometry (LC-MS/MS) instrument; and wherein the mass spectrometry is done in multiple reaction monitoring (MRM) mode or in selected ion monitoring (SIM) mode.

13. The method of claim 11, wherein at least one of $R_1$, $R_2$, or $R_3$ is methyl.

14. The method of claim 11, wherein $R_1$, $R_2$, and $R_3$ of the O-alkyl-hydroxylamine are methyl.

* * * * *